(12) United States Patent
Weber et al.

(10) Patent No.: US 12,383,437 B2
(45) Date of Patent: Aug. 12, 2025

(54) SMART ABSORBENT ARTICLES

(71) Applicants: ONTEX BV, Buggenhout (BE); ONTEX GROUP NV, Erembodegem (BE)

(72) Inventors: Ainas Weber, Bad Neuenahr-Ahrweiler (DE); Jens Hellmold, Beckum (DE); Lisa Heirman, Waasmunster (BE); Alissa Idelson, Rheinbach (DE)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 354 days.

(21) Appl. No.: 17/915,886

(22) PCT Filed: Apr. 1, 2021

(86) PCT No.: PCT/EP2021/058692
§ 371 (c)(1),
(2) Date: Sep. 29, 2022

(87) PCT Pub. No.: WO2021/198460
PCT Pub. Date: Oct. 7, 2021

(65) Prior Publication Data
US 2023/0129630 A1    Apr. 27, 2023

(30) Foreign Application Priority Data
Apr. 3, 2020 (EP) .................. 20168093

(51) Int. Cl.
*A61F 13/42* (2006.01)
*A61F 13/532* (2006.01)
(52) U.S. Cl.
CPC ............ *A61F 13/42* (2013.01); *A61F 13/532* (2013.01); *A61F 2013/422* (2013.01)

(58) Field of Classification Search
CPC ... A61F 13/42; A61F 13/532; A61F 2013/422
See application file for complete search history.

(56) References Cited

U.S. PATENT DOCUMENTS

| | | |
|---|---|---|
| 3,860,003 A | 1/1975 | Buell |
| 4,515,595 A | 5/1985 | Kievit et al. |
| (Continued) | | |

FOREIGN PATENT DOCUMENTS

| | | |
|---|---|---|
| EP | 2740450 A1 | 6/2014 |
| EP | 2496197 B1 | 8/2015 |
| (Continued) | | |

OTHER PUBLICATIONS

International Search Report and Written Opinion for PCT/EP2021/058692, mailed Jun. 14, 2021.

*Primary Examiner* — Guy K Townsend
(74) *Attorney, Agent, or Firm* — VIVICAR Law, PLLC

(57) ABSTRACT

An absorbent article for personal hygiene such as a diaper, or training pant, or incontinence insert, the absorbent article comprising: a liquid permeable topsheet; a liquid impermeable backsheet; an absorbent core positioned between said topsheet and backsheet, an indicator for indicating the presence of exudates and being positioned on a body-facing side of said backsheet, the indicator comprising an electrically conductive material, the article further comprising a detection device that can be removably attached to the absorbent article such to become in electrical communication with said indicator when attached to said article to measure a change in resistance or capacitance in response to a voiding event, wherein the absorbent core comprises a core wrap enclosing absorbent material therein and wherein a top layer of the core wrap is joined to a bottom layer of the core wrap to form one or more channels substantially free of absorbent material, and wherein the indicator comprises a (Continued)

pattern that extends inboard and/or outboard of said channel(s) such that it does not substantially overlap with said channel(s).

17 Claims, 25 Drawing Sheets

(56) References Cited

U.S. PATENT DOCUMENTS

| | | | |
|---|---|---|---|
| 4,681,793 A | 7/1987 | Linman et al. | |
| 4,710,189 A | 12/1987 | Lash | |
| 5,151,092 A | 9/1992 | Buell et al. | |
| 5,221,274 A | 6/1993 | Buell et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,865,823 A | 2/1999 | Curro | |
| 5,938,648 A | 8/1999 | Lavon et al. | |
| 6,004,306 A | 12/1999 | Robles et al. | |
| 6,093,869 A * | 7/2000 | Roe | A61F 13/42 604/385.12 |
| 6,583,722 B2 * | 6/2003 | Jeutter | A61F 13/42 340/941 |
| 6,632,504 B1 | 10/2003 | Gillespie et al. | |
| 6,946,585 B2 | 9/2005 | Brown | |
| 7,352,286 B2 * | 4/2008 | Chan | A61F 13/505 340/603 |
| 7,700,821 B2 * | 4/2010 | Ales, III | A61F 13/42 604/361 |
| 8,421,636 B2 * | 4/2013 | Collette | A61F 13/42 340/573.5 |
| 8,471,715 B2 * | 6/2013 | Solazzo | A61F 13/42 340/573.5 |
| 9,675,496 B1 * | 6/2017 | Alkhamis | A61F 13/42 |
| 10,624,795 B2 * | 4/2020 | Christiansen | A61F 13/42 |
| 11,083,636 B2 * | 8/2021 | Potter | A61F 13/42 |
| 11,173,073 B2 * | 11/2021 | MacNaughton | G08B 21/20 |
| 11,173,074 B2 * | 11/2021 | Love | A61F 13/53 |
| 11,229,557 B2 * | 1/2022 | Kurt | A61F 13/513 |
| 11,278,457 B2 * | 3/2022 | Benz | A61F 13/42 |
| 11,457,848 B2 * | 10/2022 | Harmeyer | A61B 5/369 |
| 11,617,689 B2 * | 4/2023 | Kurt | A61F 13/53 340/539.11 |
| 11,806,219 B2 * | 11/2023 | Kurt | A61F 13/513 |
| 12,178,689 B2 * | 12/2024 | Kurt | A61F 13/42 |
| 12,285,320 B2 * | 4/2025 | Love | A61G 7/05 |
| 2002/0021220 A1 * | 2/2002 | Dreyer | G09B 19/0076 340/573.1 |
| 2002/0070864 A1 * | 6/2002 | Jeutter | A61F 13/42 340/539.1 |
| 2004/0220538 A1 * | 11/2004 | Panopoulos | A61F 13/42 604/361 |
| 2007/0049883 A1 * | 3/2007 | Ales, III | A61F 13/42 604/361 |
| 2007/0083174 A1 * | 4/2007 | Ales, III | A61F 13/42 604/361 |
| 2007/0270774 A1 * | 11/2007 | Bergman | G16H 40/60 604/361 |
| 2008/0243099 A1 * | 10/2008 | Tippey | A61F 13/15699 604/361 |
| 2008/0297325 A1 * | 12/2008 | Torstensson | A61F 13/84 340/10.42 |
| 2010/0241094 A1 * | 9/2010 | Sherron | A61F 13/42 604/361 |
| 2011/0319845 A1 * | 12/2011 | Kuo | A61F 13/42 604/361 |
| 2013/0018231 A1 * | 1/2013 | Hong | A61F 13/42 600/300 |
| 2013/0036802 A1 * | 2/2013 | Johnson | A61F 13/42 73/74 |
| 2013/0076509 A1 * | 3/2013 | Ahn | A61F 13/42 340/539.12 |
| 2013/0110063 A1 * | 5/2013 | Abraham | G16H 40/67 604/361 |
| 2013/0123726 A1 * | 5/2013 | Yu | H01Q 1/273 235/492 |
| 2014/0148772 A1 * | 5/2014 | Hu | A61F 13/42 604/385.01 |
| 2014/0155850 A1 * | 6/2014 | Shah | A61F 13/42 604/361 |
| 2014/0200538 A1 * | 7/2014 | Euliano | A61F 13/42 604/361 |
| 2014/0324004 A1 * | 10/2014 | Song | B32B 5/26 436/2 |
| 2015/0080819 A1 * | 3/2015 | Charna | A61F 13/42 604/361 |
| 2015/0173968 A1 * | 6/2015 | Joseph | A61F 13/5323 604/361 |
| 2016/0310329 A1 * | 10/2016 | Patel | A61F 13/42 |
| 2017/0079858 A1 * | 3/2017 | Willhaus | A61F 13/532 |
| 2017/0156594 A1 * | 6/2017 | Stivoric | A61B 5/0008 |
| 2017/0252225 A1 * | 9/2017 | Arizti | A61F 13/42 |
| 2018/0116878 A1 * | 5/2018 | MacNaughton | G08B 21/20 |
| 2018/0263827 A1 * | 9/2018 | Omori | G06K 19/0717 |
| 2018/0333306 A1 * | 11/2018 | Ahong | A61B 5/6843 |
| 2019/0240078 A1 * | 8/2019 | Li | G01B 7/02 |
| 2019/0262191 A1 * | 8/2019 | Li | A61F 13/53 |
| 2019/0290501 A1 * | 9/2019 | LaVon | A61F 13/51401 |
| 2020/0046573 A1 * | 2/2020 | Douseki | G01N 27/416 |
| 2021/0093244 A1 * | 4/2021 | Monson | A61B 5/0022 |
| 2021/0128368 A1 * | 5/2021 | Chan | A61B 5/4318 |
| 2022/0168154 A1 * | 6/2022 | Dean | A61B 5/202 |
| 2022/0192897 A1 * | 6/2022 | Whitely | A61F 13/496 |
| 2023/0165728 A1 * | 6/2023 | Dean | G16H 40/67 604/361 |
| 2023/0293335 A1 * | 9/2023 | Hansen | A61B 5/0002 604/344 |

FOREIGN PATENT DOCUMENTS

| | | | | |
|---|---|---|---|---|
| EP | 2582341 B1 | 4/2016 | | |
| EP | 2739254 B1 | 11/2016 | | |
| EP | 3213727 A1 * | 9/2017 | | H01Q 1/243 |
| EP | 3415130 A1 | 12/2018 | | |
| EP | 3451988 B1 | 10/2020 | | |
| EP | 3747415 A1 | 12/2020 | | |
| EP | 3461257 B1 | 8/2021 | | |
| JP | 2012125452 A | 7/2012 | | |
| WO | 1995016746 A1 | 6/1995 | | |
| WO | 2008155699 A1 | 12/2008 | | |
| WO | 2011163582 A1 | 12/2011 | | |
| WO | 2012052172 A1 | 4/2012 | | |
| WO | 2018228822 A2 | 12/2018 | | |
| WO | 2018229017 A1 | 12/2018 | | |

* cited by examiner

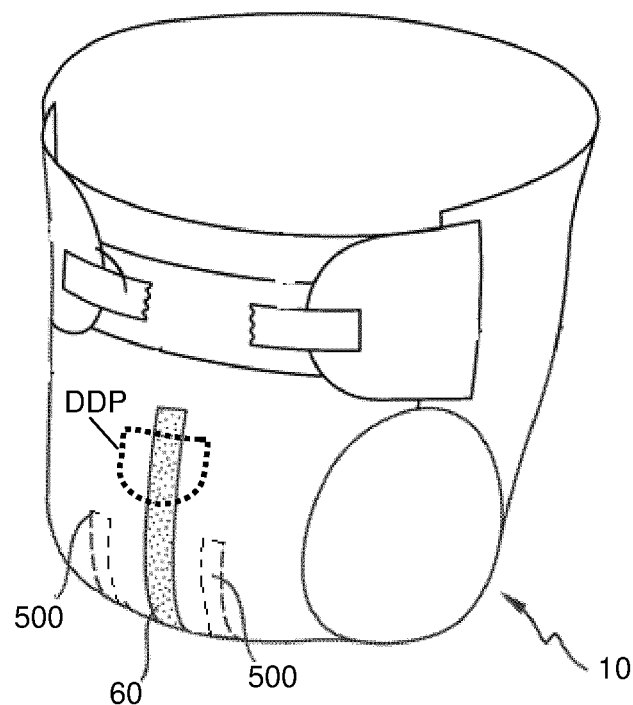
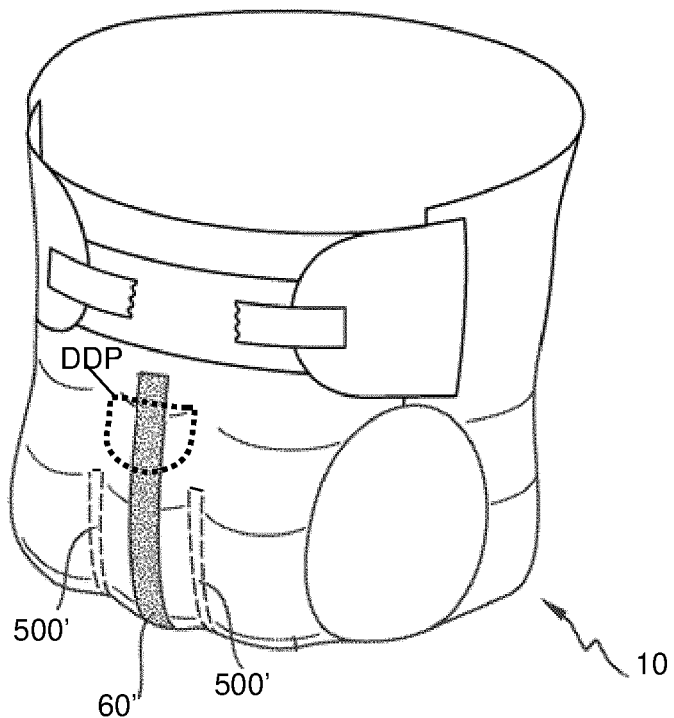
FIG.21

# SMART ABSORBENT ARTICLES

CROSS-REFERENCE TO RELATED APPLICATIONS

This application is the national stage application of corresponding international application number PCT/EP2021/058692, filed Apr. 1, 2021, which claims priority to and the benefit of European application no. 20168093.1 filed Apr. 3, 2020, which is hereby incorporated by reference in its entirety.

TECHNICAL FIELD

The present disclosure is directed to an absorbent article for personal hygiene (such as baby or adult diapers, pants or incontinence briefs or pads) and a system for monitoring thereof.

BACKGROUND

Absorbent articles for personal hygiene are designed to absorb and contain bodily exudates, such as a large quantity of urine. Non-limiting examples of disposable absorbent articles include diapers, pants, training pants, pADL, adult incontinence products, and feminine hygiene products (including, for example, sanitary napkins and tampons). Other examples of disposable absorbent articles include bandages and wound dressings. In some embodiments, for example, an absorbent article comprises several layers providing different functions, for example a topsheet, a backsheet and in-between an absorbent core, among other layers.

The function of the absorbent core is to absorb and retain the exudates for a prolonged amount of time, for example overnight for a diaper, minimize re-wet to keep the wearer dry and avoid soiling of clothes or bed sheets. The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Absorbent articles having a core consisting essentially of SAP as absorbent material (so called "airfelt-free" cores) have also been proposed but are less common than traditional mixed cores (see e.g. WO2008/155699 and WO2012/052172).

A number of disclosures exist (see for example EP2496197B1, EP2739254B1, and EP2582341B1) directed to sensors to sense a condition such as temperature from body or moisture from incontinence. The sensor comprises a signal processing unit, a transmitter and a power supply, typically in form of a battery. These elements are arranged on a flexible substrate in low profile enabling disposition adjacent to the human body. A complex series of mathematical and statistical manipulations are then needed in order to determine wetness events and wetness levels.

While such devices allow monitoring conditions of the human body and can also be used as a moisture sensor, it represents also relatively costly solution. It would not be seen appropriate to dispose of the sensor together with a (disposable) absorbent article. If the sensor, however, is to be reused, the sensing area has potentially been exposed to moisture. Therefore this concept does not allow for simple usage.

Examples of articles that provide improvements to the above drawbacks are disclosed in EP3415130, WO/2018/228822, WO/2018/229017, EP3461257, and EP3451988.

Moreover improved incontinence management systems are for example described on co-pending application EP19178665.6.

A need nevertheless exists for improved monitoring devices especially those having fluid distribution enhancing features such as channels.

A need also exists to provide an environmentally friendly solution for automatic voiding pattern detection preferably that can be further used to monitor the babies development or an adult's incontinence pattern and/or risk of leakage.

SUMMARY

In a first aspect the disclosure relates to an absorbent article for personal hygiene such as a diaper, or training pant, or incontinence insert, the absorbent article comprising: a liquid permeable topsheet; a liquid impermeable backsheet; an absorbent core positioned between said topsheet and backsheet, an indicator for indicating the presence of exudates and being positioned on a body-facing side of said backsheet, the indicator comprising an electrically conductive material, the article further comprising a detection device that can be removably attached to the absorbent article such to become in electrical communication with said indicator when attached to said article to measure a change in resistance or capacitance in response to a voiding event, wherein the absorbent core comprises a core wrap enclosing absorbent material therein and wherein a top layer of the core wrap is joined to a bottom layer of the core wrap to form one or more channels substantially free of absorbent material, and wherein the indicator comprises a pattern that extends inboard and/or outboard of said channel(s) such that it does not substantially overlap with said channel(s).

In a second aspect the disclosure relates to a kit comprising an absorbent article and a detection device, wherein the kit comprises a plurality of the absorbent articles and a detection device, wherein the detection device is removably attached to the absorbent articles, one after another as they are used, and wherein the detection device is arranged to stop working after a predetermined period of time, preferably wherein the predetermined period of time is more than 20 days and less than 50 days, more preferably from 30 days to 40 days.

BRIEF DESCRIPTION OF THE FIGURES

FIG. 21 is a perspective view of the taped diaper according to embodiments herein as it may appear when worn before and after loading.

DETAILED DESCRIPTION

Figure 1:
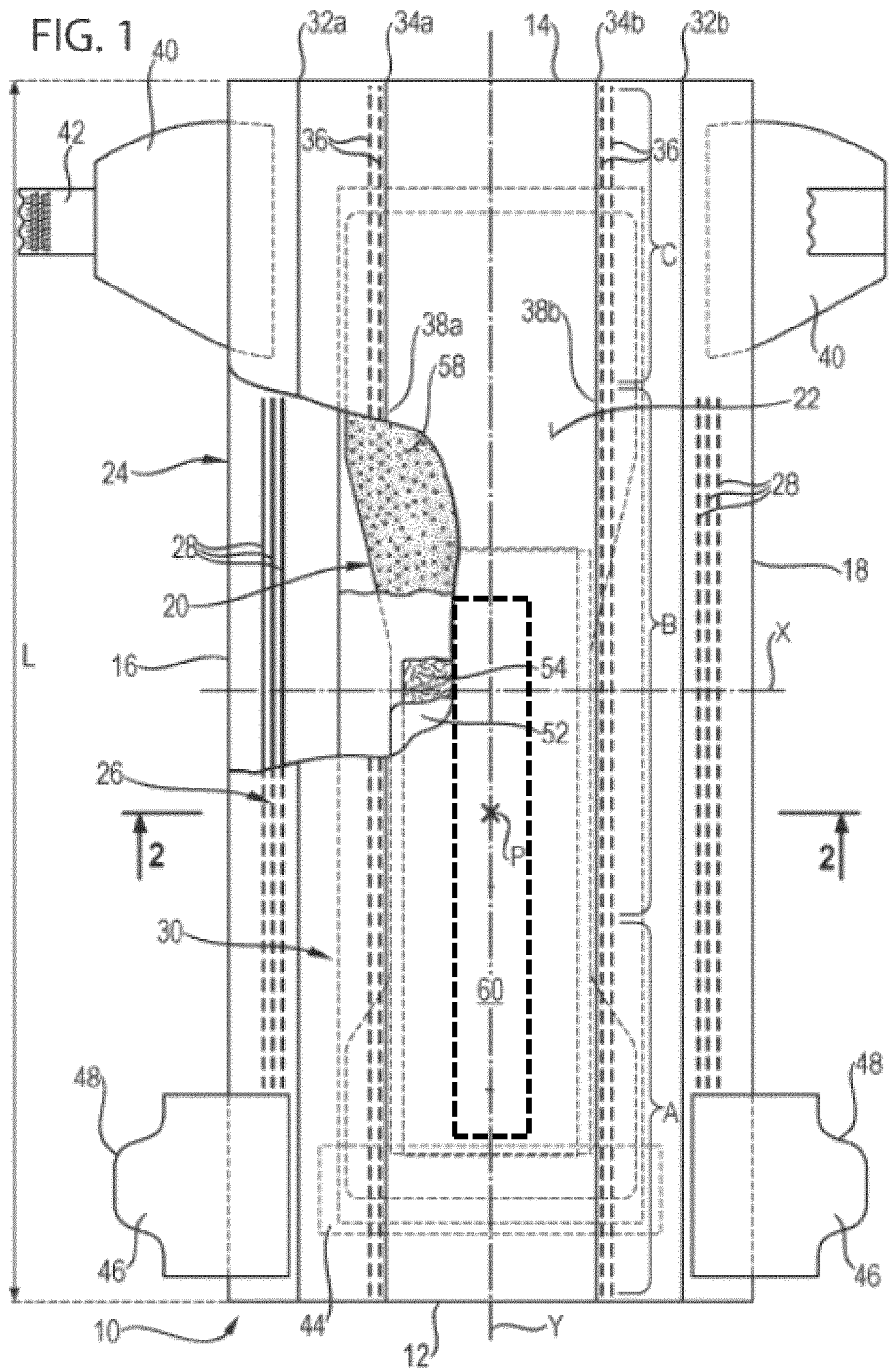
FIG. 1 is a top view of an absorbent article according to an embodiment of the present disclosure in the form of a diaper with some layers partially removed.

Unless otherwise defined, all terms used in disclosing characteristics of the disclosure, including technical and scientific terms, have the meaning as commonly understood by one of ordinary skill in the art to which this disclosure belongs. By means of further guidance, term definitions are included to better appreciate the teaching of the present disclosure.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed disclosure. However, it is to be understood that the value to which the modifier "about" refers is itself also specifically disclosed.

The expression "% by weight" (weight percent), here and throughout the description unless otherwise defined, refers to the relative weight of the respective component based on the overall weight of the formulation.

The recitation of numerical ranges by endpoints includes all numbers and fractions subsumed within that range, as well as the recited endpoints unless otherwise stated.

As used herein, the "skin facing", "body-facing" or "bodyside" surface means that surface of the article or component which is intended to be disposed toward or placed adjacent to the body of the wearer during ordinary use, while the "outward", "outward-facing" or "garment-side" or "garment facing" surface is on the opposite side, and is intended to be disposed to face away from the wearer's body during ordinary use. Such outward surface may be arranged to face toward or placed adjacent to the wearer's garments or undergarments when the absorbent article is worn.

As used herein "channels" are fluid distribution means within the absorbent core adapted to favour exudate flow therealong and are typically intended to exclude embossing patterns or ducts formed by compression and rather include structures that are substantially free of absorbent material instead of comprising compacted absorbent material. Channels herein can be formed by joining upper and lower layers of a core wrap as will be described in more detail hereinbelow or may be achieved by removing absorbent material such as by cutting.

As used herein, the term "absorbent article" refers to disposable devices such as infant or adult diapers or pads, pants, training pants, and the like which are placed against or in proximity to the body of the wearer to absorb and contain the various exudates discharged from the body. Typically these articles comprise a topsheet, backsheet, an absorbent core and optionally an acquisition system (which may be comprised of one or several layers) and typically other components, with the absorbent core normally placed between the backsheet and the acquisition system or topsheet.

The absorbent articles of the disclosure will be further illustrated in the below description and in the Figures in the form of a taped diaper, though all embodiments described herein may equally be applied onto absorbent articles in the form of pants (or even in the form of feminine hygiene or incontinence liners). Nothing in this description should be however considered limiting the scope of the claims unless explicitly indicated otherwise. Unless indicated otherwise, the description refers to the dry article, i.e. before use and conditioned at least 24 hours at 21° C.+/−2° C. and 50+/−20% Relative Humidity (RH).

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m2 or gsm).

The terms "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element. The terms further include embodiments in which a pocket or other connector is formed in or attached to an area of the absorbent article. Further, these terms include configurations in which the elements are removably, or non-removably, joined, bonded, or attached. For example, wherein an element is described as "joined" within the configuration, it may be either removably joined or non-removably joined unless otherwise specified or evident from the context.

The terms "comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

By "absorbent material" it is meant a material which has some absorbency property or liquid retaining properties, such as SAP, cellulosic fibers as well as synthetic fibers, most preferably is selected from the group consisting of SAP, cellulose (or cellulosic) fibers, and mixtures thereof. Herein, absorbent materials in the form of fibrous absorbent materials have been found to be useful. These fibrous absorbent materials can comprise or consist of natural fibers, e.g. cellulosic fibers as well as synthetic fibers. Typically, glues used in making absorbent cores have no absorbency properties and are not considered as absorbent material.

As used herein, the term "absorbent core" refers to the component or components of the article having the most absorbent capacity and comprising an absorbent material and optionally a core wrap enclosing the absorbent material. The term "absorbent core" does not include the acquisition-distribution system or layer or any other component of the article which is not either integral part of the core wrap or placed within the core wrap. The core may consist essentially of, or consist of, a core wrap, absorbent material as defined below and glue enclosed within the core wrap.

The values indicated herein are measured according to the methods indicated herein below, unless specified otherwise. All measurements are performed at 21±2° C. and 50±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

The Absorbent Article

Absorbent articles herein are for personal hygiene such as a diaper, or training pant, or incontinence insert, the absorbent article comprising: a liquid permeable topsheet 22; a liquid impermeable backsheet 24; an absorbent core 20 positioned between said topsheet 22 and backsheet 24, an indicator 60 for indicating the presence of exudates and being positioned on a body-facing side of said backsheet 24, the indicator 60 comprising an electrically conductive material, the article further comprising a detection device 70 that can be removably attached to the absorbent article such to become in electrical communication with said indicator 60 when attached to said article to measure a change in resistance or capacitance in response to a voiding event, wherein the absorbent core 20 comprises a core wrap 66 enclosing absorbent material therein and wherein a top layer 66*a* of the core wrap 66 is joined to a bottom layer 66*b* of the core wrap 66 to form one or more channels 500 substantially free of absorbent material, and wherein the indicator 60 comprises a pattern that extends inboard and/or outboard of said channel(s) such that it does not substantially overlap with said channel(s). Typically wherein the channels(s) extend from 10% to 95% of a length of the core 20 such that said channel(s) are surrounded by absorbent material. Advantageously this arrangement allows for accurate exudate detection and position determination when liquid distributing channels are present in the core, indeed it has been found that in order to accurately determine position of soiling within the absorbent article, it is beneficial to ensure that the conductive layers of the indicator do not overlap the channels that are quickly immediately soiled with exudates in moments of time immediately following a voiding event.

The absorbent article may comprises one or more indicator(s) adapted to indicate the presence and/or absence of bodily exudates and/or determine saturation level and when the article should be replaced with a new clean one. The indicator, in some embodiments, for example, may comprise an indicator that reacts to the presence and/or absence of bodily exudate(s) and/or one or more properties of those bodily exudate(s) within the absorbent article via one or more change in property of the indicator (e.g., a physical, chemical or biological property such as color, smell, sound, pH, or the like). One or more property or state of the indicator, in turn, may be detected by a detector device physically and/or communicatively coupled to the absorbent article. In one particular implementation, for example, the indicator comprises an optical property changing composition or device (e.g., a color-changing composition or device, such as a color changing indicator) that changes an optical property (e.g., color) in response to a variation of pH associated with the presence and/or absence of bodily exudates within the absorbent article). The indicator might also comprise one or more additional indicators of the same or different type that provide different types of indications and/or indications of bodily exudates (or properties of bodily exudates) detected in one or more different regions of the absorbent article. In one embodiment, for example, a second electrical indicator may comprise a resistance, capacitance, inductance or continuity sensitive indicator. Alternatively, such electrical indicators may be provided as an alternative or in conjunction with optical indicators. A resistance sensitive indicator can be provided, for example, by providing two or more electrical conductors disposed at a given spatial distance relative to each other. If bodily exudates, which typically comprise a liquid portion, come in contact with the two electrical conductors, the resistance between the two electrical conductors is reduced (examples of this arrangement are described in more detail in applicant's prior disclosures such as EP3415130, WO/2018/228822, WO/2018/229017, EP3461257, and EP3451988). Other indicators, as known in the field in the context for sensor for absorbent articles, can also be useful. In one particular embodiment, for example, the multiple property changing indicators may be provided in the same or different locations within the absorbent article. For example, an optical property changing indicator (e.g., color changing indicator) may be disposed in a first location of an absorbent article and a second property changing indicator that is the same or a different type of indicator (e.g., another optical property changing indicator such as a color changing indicator) may be disposed in a second location of the absorbent article.

The absorbent article and the one or more indicators are provided to form an integral unit. For forming the integral unit, the indicator(s) can be directly or indirectly attached to the absorbent article. Direct or indirect attachment to the article is typically to one or more distinguishable element of the article. For example, it can be useful to attach the indicator(s) to the back sheet of the article, such that the indicator(s) and the back sheet of the article from one integral unit. For example if the indicator(s) are provided in sheet form, the respective sheet can be adhesively attached to the back sheet of the article. The respective sheet could also be provided from one and the same material with the back sheet, this material however being treated in suitable ways as to provide an indicator in a pre-defined area (for example by printing an electrically conductive material on a skin or body facing side of the liquid impermeable backsheet layer).

According to one particular embodiment, a detector device (herein also referred to a clip-on processing unit or clip-on unit) is also provided. The detector device, in this implementation, comprises a housing and is adapted to be physically coupled to the absorbent article such that the detector device is further communicatively coupled to one or more indicator integral with the absorbent article. The detector device and/or the absorbent article may comprise one or more connector for removably joining the detector device with the absorbent article. The connector(s) are provided such that the detector device can be attached to the absorbent article and can be detached from the absorbent article including the one or more indicator(s). The detector device can be attached to the integral unit and can be detached from the integral unit. In one particular embodiment, for example, the detector device can be attached to an area of the absorbent article juxtaposed the indicator integral to the absorbent article, and can be detached from that area of the absorbent article so as to be removably connectable thereto.

The housing of the detector device, in one embodiment, has an outer extension in a first direction and an outer extension in a second direction, which is perpendicular to the first direction. The first direction, in this embodiment, may be chosen as characteristic directions, e.g. along a main axis and normally as that of largest extension of the housing. For safety and convenient handling of the device, it may be useful that the device has a length in the first direction of at least 3 cm, 4 cm or more (but normally less than 10 cm) and that the device has a length in the second direction of at least 2 cm, 3 cm or more (but normally less than 10 cm). In one particular embodiment, for example, the housing has a first dimension of at least about 4 cm and a second dimension of at least about 8 cm. In various embodiments, the housing can be rigid or at least partially or fully flexible. To be flexible the detector device can incorporate flexible electronic components (and boards).

According to one embodiment, the detector device comprises one or more optical sensor, such as a color sensor. This optical sensor can generate an output which depends on an optical property (e.g., a color) observed by the optical sensor. Some examples of optical sensors across a range of wavelengths are: electron tube detectors, photosensors, photomultiplier tubes, phototubes, photodetectors, opto-semiconductor detectors, photodiodes, photomultipliers, image sensors, infrared detectors, thermal sensors, illuminance sensors, visible light sensors and color sensors. In one particular embodiment, for example, the optical sensor may comprise a photodiode such as a TCS 34725 color sensor commercially available from AMS-TAOS USA Inc.

In other embodiments, for example, the detector device need not include a light source, such as where sufficient ambient light may be provided in an application, where light is provided elsewhere (e.g., associated with an absorbent article or clothing, or elsewhere in an environment) or where the property change of a property changing indicator may be detectable without light, such as resistance, impedance and/or capacitance measurements when the indicator comprises an electrically conductive material (such as a conductive ink).

Often, the detector device will also comprise one or more light, such as a light emitting diode (LED), organic light emitting diode (OLED), an incandescent light bulb, thermionic light emission, luminescence (e.g., among others, fluorescence, chemilluminescence, electroluminescence (e.g., LED), for emitting light onto an area, the wavelength or spectrum of which is to be assessed by the optical sensor. The optical sensor in some color detecting embodiments can be optimized for assessing a color of a color-changing indicator. The optical sensor can be sensitive to visible and non-visible light, namely light in the near IR range. In various embodiments, UV, visible infrared and near infrared wavelengths may be used. A color changing indicator can change its color, for example, based on the presence and/or absence of bodily exudates and/or in response to some other condition being monitored with respect to the absorbent article. In this embodiment, the color sensor can provide an output that varies depending on the presence or absence of bodily exudates.

In a preferred embodiment, an LED is used as light emitting source. Preferably, at least two light sources are emitted comprising a first color and a second color wherein the first color is different from the second color. Typically wherein the first color corresponds to a color that is most absorbed in a first state of the indicator and the second color corresponds to the color that is most absorbed by the indicator in a transition state. For example, the first color may be blue (this is particularly useful if the indicator is for example yellow in dry state) and the second color may be selected from red (this is particularly useful if the indicator is fore example green in a transition state).

In a particularly preferred embodiment, the indicator 60 is a color-changing indicator that changes color in response to a voiding event, such as an exudate wetness event, and wherein said indicator 60 has the following colors: substantially yellow in dry state, substantially blue in a fully saturated wet state, and is substantially green in a transition state between said dry state and said fully saturated wet state. These types of indicators, that will be described in further detail herein, have the advantage that when using Blue and Red LEDs a more accurate and energy efficient detection of wetness degree in the absorbent article can be determined. In fact, as discussed above when the indicator is yellow it will absorb mostly blue light and when the indicator is blue it will absorb mostly red light, but moreover when the indicator is in its green transition phase it will absorb both red and blue light, thus the specific selection of a Blue LED source and a Red LED source allows to accurately determine (by use of optical sensors as described herein) at least three conditions on the absorbent article: a dry state; a partly wet state; and a wet/saturated state. All this will be determined in a cost effective way and whilst limiting power usage by using color LEDs as described on more detail hereinbelow.

In an embodiment, the light source may comprise a Blue LED, a Red LED, and a White LED.

In view of the above, in an embodiment, the LED source comprises a first color being green, a second color being red and a third color being blue. Advantageously, this combination of colors ensure to allow detection of any changes of any color change of the indicator thus allowing flexibility in choice of color changes by the indicator.

In an embodiment, the light emitting source does not comprise a white color LED, indeed white LEDs have been found to consume more energy and thus significantly reduce the battery life of the clip-on units (or detection devices or detector devices) herein, advantageously color sources like Blue and Red LEDs use less energy and can thus increase the battery life without having to increase size of the battery and thus size of the overall detection device (herein also referred to as detector device).

In a preferred embodiment, the optical sensor comprises an RGB (Red, Green and Blue) optical sensor and preferably further a Light Dependent Resistor (LDR). The former setup identifies colour variations while the latter detects intensity changes in the whole spectrum. The data acquisition may be realised by means of an Analog-to-Digital Converter (ADC) e.g. an Arduino, which sends the information to a processor via for example a continuous data link.

In various embodiments, essentially any known color-changing indicator that responds to the absence or presence of bodily exudates or other conditions to be monitored with respect to the absorbent article can be useful. It may be useful to employ a color-changing indicator which comprises a chemical substance. Such a chemical substance can induce a color change when bodily exudates are present. One useful form of a color-changing indicator comprises a pH-sensitive indicator. Bodily exudates, for example, may influence the pH-value in their environment. Similarly, components within an absorbent article may alter a pH of the environment in response to contact with one or more bodily exudates. In one particular embodiment, for example, as AGM swells in the presence of urine or other liquids present in a bodily exudate, the AGM swelling changes the pH of the environment within the absorbent article. Thus, in this and other embodiments, a pH-sensitive indicator can be used and detected by the detector device.

Other useful indicators can comprise biological or physical sensor materials. The skilled person is aware of numerous useful biological sensor materials. Physical sensors can be provided by a material, which changes its color when the material is stretched. Stretching of a material can be induced by the swelling of the absorbent core. Biological sensors may include a bioreceptor that interacts with an analyte of interest, such as trypsin or urease. A bioreceptor, for example, may use reagent/analyte interactions that provide a property change (e.g., a color or other optical change) in the absorbent article upon detection of a particular analyte of interest. In one particular embodiment, for example, a bioreceptor may use an immobilised binding reagent also capable of binding to an analyte of interest. The immobilized reagent for example, may be disposed at a detection zone detectable by a sensor of a detector device.

Additionally the indicator can comprise a material selected from the group comprising, consisting essentially of or consisting of: thermochromic inks, thermochromic dyes, thermochromic liquid crystalline materials, and combinations thereof. These indicators can, for example, serve to monitor other conditions associated with the absorbent article and/or wearer of the absorbent article, such as body temperature or fever indication.

The present embodiments can usefully employ one or more connectors which allow for detachment and can also allow for refastening of an indication device to the absorbent article. Such connectors may comprise one or more adhesives or cohesives. Such connectors may further comprise one or more mechanical fasteners, including strap based fasteners or fasteners comprising at least one button or at least one magnet. Among the group of mechanical fasteners, a hook-end-loop fastener is useful. It can be useful to attach the hook-portion to the absorbent article or to attach the loop-portion to the absorbent article. The corresponding portion can then be attached to the detector device.

In one useful embodiment, the loop portion of a hook-and-loop-fastener can be provided integral with the absorbent article. For example, if the outer side of the backsheet of the absorbent article is provided from a textile material, e.g. a non-woven material, loops provided in such a material can interact with the hooks of a hook-portion of a fastener.

There are also alternative forms of mechanical fasteners (to be used as connectors), which can be used additionally or alternatively. For example, a pocket can be formed in an area of the absorbent article. For example, such a pocket can be formed between layers of the backsheet. A pocket can also be formed between other layers. For example, diapers can be provided as pant-diapers comprising a crotch-portion and a belt-portion. The crotch-portion and the belt-portion can be joined adhesively or mechanically, e.g. by crimping. In the area of adhesive joining, a certain portion can be free of adhesive and accessible from the outside. This portion can than serve as a pocket for receiving the detector device. A belt, strap or other device may be used to place and hold the detector device relative to the absorbent article. The detector device may similarly be joined or held to an article of clothing worn by the user wearing the absorbent article by mechanical means or otherwise.

The detector device provides information which in one aspect will indicate the presence and/or absence of bodily exudates. Such a detector device can comprise a variety of output and/or display elements. A simple output element can comprise LED, OLED or similar lamps. For example a green light can be used as an indication for the absence of bodily exudates or presence only a low amount of bodily exudates whereas a red light can indicate the presence of a higher amount of bodily exudates and therefore will normally indicate the need to change the absorbent article. Information can be provided in more comprehensive forms and therefore a display element, for example in the form of a small monitor can be useful. Information to be displayed on such a monitor or similar display element could include information about the loading status of the absorbent article, the time at which a fresh absorbent article has been applied and so forth.

The output element or display element can be provided within the housing or attached to the detector device. The output element, for example, may include a visual output device (e.g., display, LED or the like), an audible output device (e.g., a speaker), a tactile output device and/or the like.

The output or display element can also be provided in a separate unit. Such a separate unit can also have other functions. It can be useful to employ a mobile phone with a display or another personal digital assistant for use as a display element in the present context. The display element can also be a computer (including a laptop computer or a tablet computer). Information obtained from the detector device can also be displayed on several such units at the same time. This can be displayed there in the same format or in similar formats. For example a more detailed display of information on a computer can be combined with simplified display of information on a mobile phone. Additionally or alternatively the output element can also comprise acoustic indication device and can also rely on a computer generated voice. In some cases also, the information is not or not only displayed or provided, but directed to a data storage device for data aggregation.

In one particular implementation, the separate unit may include any display or output device in the area surrounding the detector device (e.g., within a house, apartment or the like). The separate unit may further include a plurality of input/output nodes that may be communicatively coupled to the detector, such as an Amazon® Echo® device that may provide visual and/or audio outputs (e.g., "diaper needs changing").

For providing information to the separate unit the detector device can broadcast or otherwise send information to the unit comprising the display element. The skilled person is aware of useful standards for providing such broadcasting, for example Bluetooth, BTLE, mesh (e.g., IEEE 802.15.4), WiFi (e.g., IEEE 802.15.11), communication incorporating all or any portion of IEEE 802 or similar communication standards, RFID, 3G or 4G communication, Backscatter communication, light communication, audio/sound communication, harvesting protocol communication (e.g., a metadata harvesting protocol). Other communications protocols or combinations of communications protocols (e.g., a Bluetooth/Mesh combined protocol) can be employed. Additionally or alternatively an acoustic or optical broadcasting is useful.

In a further embodiment, a kit comprising a multitude of absorbent articles and a detector device, which comprises a housing and a connector, such that the detector device can be connected to any one of the absorbent articles is also provided. The absorbent articles and the detector device may each comprise any of the further features described herein. Hence, the detector device can be used on a first absorbent article of the multitude, the absorbent article can be disposed of after use, and the detector device can be re-used on another (fresh) absorbent article.

Figure 2:
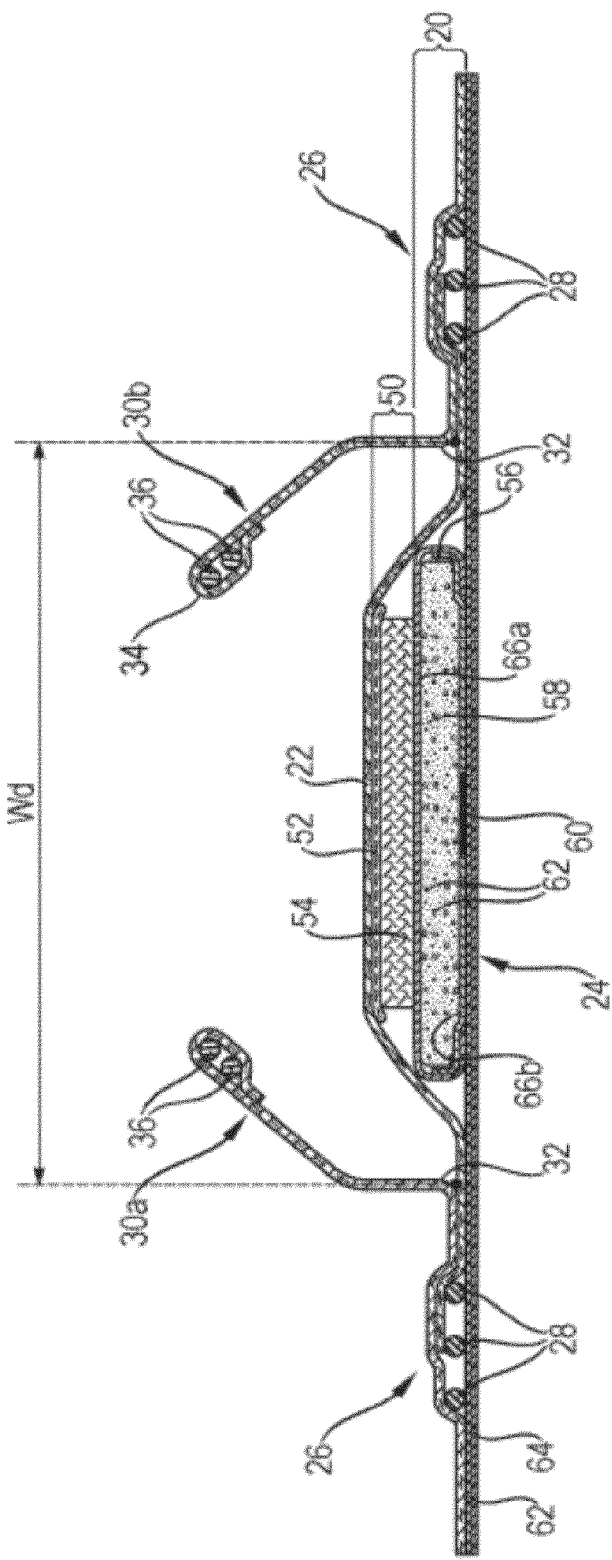
FIG. 2 is a transversal cross-section of the embodiment of FIG. 1 at the crotch area.

An exemplary absorbent article according to one embodiment in the form of an infant diaper 10 is represented in FIGS. 1 and 2, although it is understood herein that equally adult diapers and pants may be suitable herein.

FIG. 1 is a plan view of the exemplary diaper 10, in a flattened state, with portions of the structure being cut-away to more clearly show the construction of the diaper 10. This diaper 10 is shown for illustration purpose only as many embodiments may use a wide variety of diapers or other absorbent articles. The diaper extends from a front edge 12 to a longitudinally opposed rear edge 14. It comprises left side edge 16 and transversally opposed right side edge 18. The diaper 10 comprises an absorbent core which is positioned between topsheet 22, which is at least partially liquid permeable and backsheet 24, which is essentially impermeable to liquid.

In FIG. 1 "X" denotes a transversal access through the geometrical center of the diaper, and axis "Y" denotes the longitudinal direction. The area A denotes the front area of the diaper as seen in the longitudinal direction and C denotes the rear area of the diaper as seen in the longitudinal direction, and B denotes the central area or crotch area positioned between area A and area B, in the longitudinal direction. L denotes the length of the diaper from the front edge 12 to rear edge 14 as measured in the longitudinal direction.

The article comprises a crotch point P defined herein as the point placed on the longitudinal axis at a distance of two fifth (⅖) of L starting from the front edge 12 of the diaper 10.

The absorbent article comprises an indication means 60, which can take the form of a small sheet of material or patch. As shown, a rectangular form is useful. The indication means 60 can be arranged in the front area A, the central area B or the rear area C of the diaper. It is often useful to arrange the indication means 60 in the central area B and in the front area A. As shown, it can be useful to provide the indication means 60 towards the front of the crotch point P and preferably on at least a portion of the central area B.

The diaper 10 may further comprise gasketing cuffs 26 for maintaining a tight fit of the diaper 10 to the wearer, when the diaper 10 is worn. The gasketing cuffs 26 comprise elastics 28 for maintaining the tight fit, which helps to avoid leakage.

The diaper 10 may further comprise barrier leg cuffs 30 on each side of the diaper. Barrier leg cuffs comprise proximal edges 32a and 32b, which are adjacent to topsheet 22. Opposed to the respective proximal edges, the barrier leg cuffs 30 comprise distal edges 34a and 34b, respectively. In the area of the distal edges 34, further elastics 36a provided, while a portion of the distal edges 34 of the barrier leg cuffs 30 can be attached to components of the diaper 10, such as the topsheet 22, it is preferred that the barrier leg cuffs 30 also comprise unattached areas of the distal edges, herein referred to as free flaps 38. The respective free flaps 38 are typically provided in the central zone of the diaper 10.

The diaper 10 may further comprise the fastening system, for fastening the diaper to the body of a wearer. This fastening system comprises two back ears 40, which comprise adhesive tapes 42. The adhesive tapes 42 can be attached to landing zone 44. In the front area, the diaper comprises front ears 46. As described below, for other embodiments other fastening systems can be useful, including mechanical fasteners and including fastening systems comprising more than two, for example for IS.

In a preferred embodiment, the indicator 60 has a longest length parallel to the longitudinal axis Y and a shortest width perpendicular thereto, and wherein said indicator is positioned asymmetrically along the absorbent article (e.g. diaper 10) length such that it overlaps the transverse centreline X of the diaper 10 and the distance between said transverse centreline X and a position of the indicator 60 closest to the back edge 14 is smaller than the distance between said transverse centreline X and a position of the indictor closest to the front edge 12, as for example shown in FIG. 1.

Advantageously, this allows the indicator to be easily viewed by a caregiver and to allow accurate detection of saturation as well as being functionally operable with a detection device as will be described in more detail hereinbelow, whilst at the same time limiting cost and unnecessary material waste.

The core can optionally comprise areas, where there is a reduced amount of absorbent material or no absorbent material. These areas are referred to as channels. The channels are typically formed by joining together top and bottom core wrap layers, wherein the core wrap encloses the absorbent material therein except in the channel regions.

Figure 18:
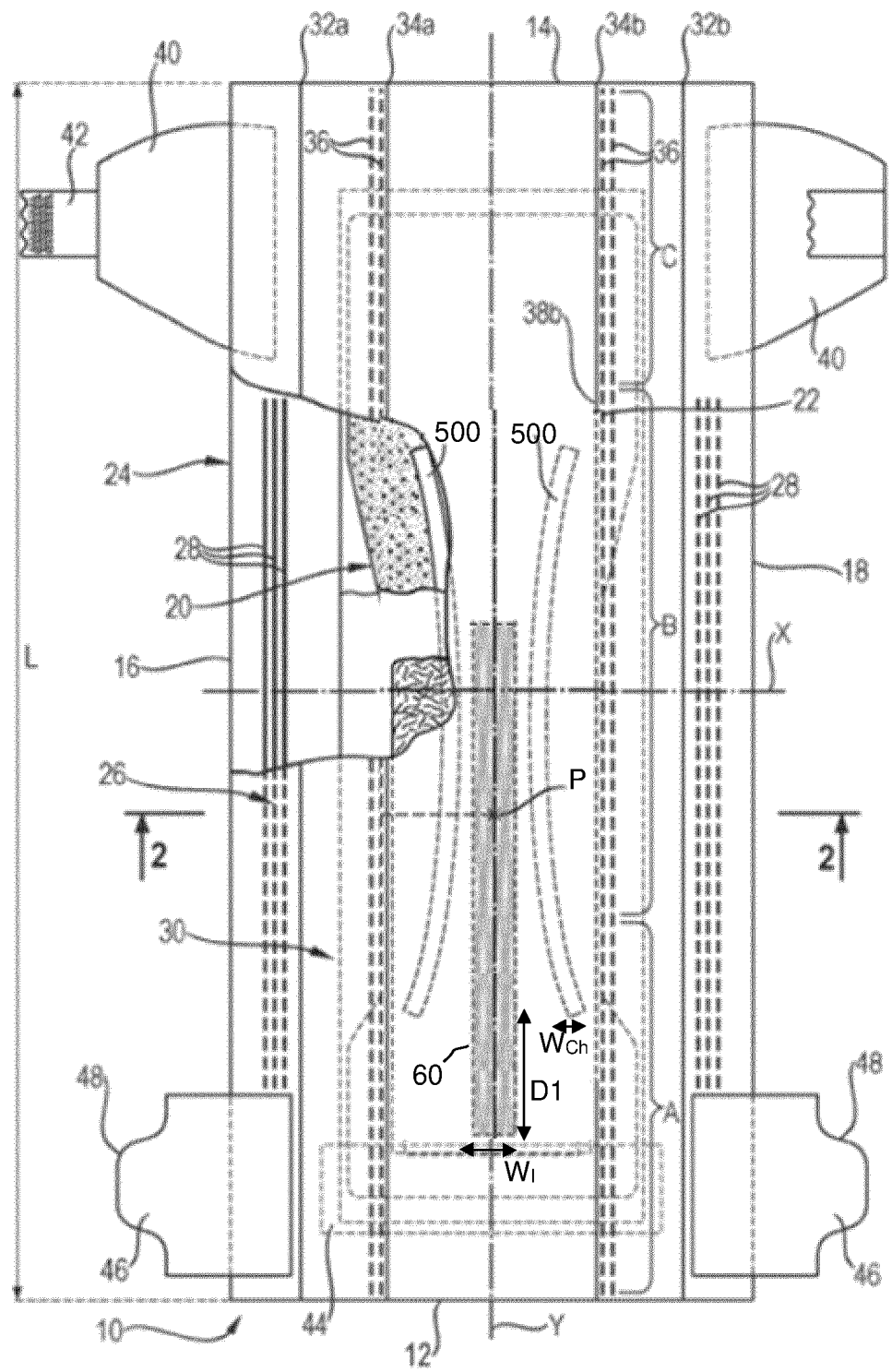
FIG. 18 is a top view of an absorbent article according to an embodiment of the present disclosure in the form of a diaper with some layers partially removed.

As illustrated in exemplary FIG. 18, the core may comprise a plurality of channels 500, preferably two channels 500. Typically the channels 500 comprise at least one right channel and at least one left channel, the right channel being disposed between the right side edge 18 and the longitudinal centreline along axis Y, and the left channel being disposed between the left side edge 16 and the longitudinal centreline along axis Y. The right and left channels may be arcuate in shape such that the front and back ends of the left and right channels diverge towards the left side edge 16 and the transversely opposed right side edge 18 respectively and typically wherein the central portion of said channels converge towards the longitudinal centreline along axis Y.

In an embodiment, the pattern of the indicator 60 comprises a plurality of sensing tracks 520 each track forming an open circuit corresponding to a different position of the backseat 24 and the absorbent core (20) such that voiding events in said different positions may be individually monitored. The different positions corresponding to at least two of: a front A, crotch B or back C portions of the article. Advantageously this allows for detection of exudates when a wearer is in various positions such as standing, lying on the back or on the belly as exudates will flow generally in the direction of gravity such that accurate monitoring of risk of leakage and/or warnings to change wearer's position can be triggered.

In an embodiment, each of the sensing tracks 520 comprises a connection end 521 arranged to couple to a respective terminal end of the detection device 70 to form an electrical connection between said detection device 70 and said sensing tracks 520 of the indicator.

Preferably, the sensing tracks 520 are printed with a conductive ink.

Preferably, wherein the conductive ink is a carbon-based ink and/or a conductive polymer-based ink.

In an embodiment, the carbon-based ink comprises a conductive compound selected from the group consisting of graphene, graphite, nano-carbon-tubes and mixtures thereof.

In an embodiment, the conductive polymer-based ink comprises a polymer selected from the group consisting of polyacetylene, polypyrrole, polyaniline and copolymers thereof, more preferably selected from the group consisting of poly(pyrrole)s (PPY), polyanilines (PANI), poly(thiophene)s (PT), poly(p-phenylene sulfide) (PPS), poly(p-phenylene) (PPP), Poly(acetylene)s (PAC), Poly(p-phenylene vinylene) (PPV), poly(3,4-ethylenedioxythiophene) (PEDOT), and mixtures thereof, most preferred conductive polymer-based ink comprising poly(3,4-ethylenedioxythiophene) polystyrene sulfonate (PEDOT:PSS).

Preferably, the indicator (60) is free of metals.

When channels are present, the indicator 60 may extend therebetween along the Y axis and is arranged such that it prolongs beyond the channels 500 at a first distance D1 towards front edge 12. Preferably, the indicator 60 comprises a rear terminal edge (being the portion of said indicator 60 closest to the back or rear edge 14) positioned between said channels 500 generally such that it does not prolong beyond the channels 500 towards the rear edge 14. Advantageously, the detector device may thus be placed on the front of the article with limited risk of faulty or premature warnings due to early saturation of regions of the core proximal to the channels that would otherwise cause the indicator to change color too soon prior to real saturation across the majority of the core.

In a preferred embodiment, the channels 500 have a width $W_{Ch}$ (typically in a dimension substantially parallel to the transverse axis X) and the indicator 60 has a width $W_I$ (typically in a dimension substantially parallel to the transverse axis X), wherein $W_I$ is greater than $W_{Ch}$, preferably wherein $W_I$ is from $1.1 W_{Ch}$ to $4W_{Ch}$, more preferably from $1.2W_{Ch}$ to $3W_{Ch}$, even more preferably from $1.3W_{Ch}$ to $2.5W_{Ch}$, even more preferably from $1.4W_{Ch}$ to $2.2W_{Ch}$, even more preferably from $1.5W_{Ch}$ to $2.0W_{Ch}$. Without wishing to be bound by theory, a larger width of the indicator is beneficial in order to ensure correct reading from the detector device and to limit any lateral light refractions on surfaces not covered by the indicator, however if the indicator width is too great it may negatively impact accuracy of the wetness determination as it approaches or even overlaps the channels that are designed to quickly transport liquid. A balance has therefore been determined between the channel width and indicator width that provides for stable detection and limit false warnings/alarms.

The width $W_{Ch}$ of channels herein may vary depending on the absorbent article (e.g. diaper) size, nevertheless typically is in the range of from 5 mm to 30 mm, preferably from 7 mm to 25 mm, even more preferably from 9 mm to 20 mm, even more preferably from 10 mm to 15 mm. Such measurements are typically taken from a dry-state diaper prior to it being wetted.

In an embodiment, the distance between the indicator 60 and a position of a channel 500 closest thereto is less than indicator width $W_I$ and is equal to or greater than the channel width $W_{Ch}$. Typically the position where the one or more channels 500 are closest to the indicator 60 is proximal to the rear terminal edge of the indicator 60 and distal from a position where the detection device is to be coupled. It has been found that even in portions of the indicator distal from where the detection device is to be connected, it is desirable to ensure a certain spacing between the indicator and the channels whilst at the same time being close enough to start triggering a change (e.g. of color) from positions proximal to the rear terminal edge towards the front edge of the indicator where the detection device is to be positioned.

In an embodiment, the distance D1 between a front-most edge of the one or more channels 500 and a front-most edge of the indicator 60 is more than $2.0W_{Ch}$, preferably from $2.5W_{Ch}$ to $10.0W_{Ch}$, more preferably from $3.0W_{Ch}$ to $8.0W_{Ch}$, even more preferably from $3.5W_{Ch}$ to $7.0W_{Ch}$, even more preferably from $4.0W_{Ch}$ to $6.0W_{Ch}$, even more preferably from $4.5W_{Ch}$ to $5.5W_{Ch}$. The width of the channels has been found to affect the speed of liquid distribution along the core view of the absence of absorbent material therein, it is therefore beneficial for the indicator to extend further away from the apex of the channels to a position proximal to the front of the absorbent article where the detection device is to be connected (the detection device position DDP). Below the mentioned lower ratios, risk of premature warning before actual saturation of the diaper is very high, and above the mentioned upper ratios the risk of delayed warning is very high (e.g. too much time for the indicator at the detection device position DDP to change color).

Figure 19:
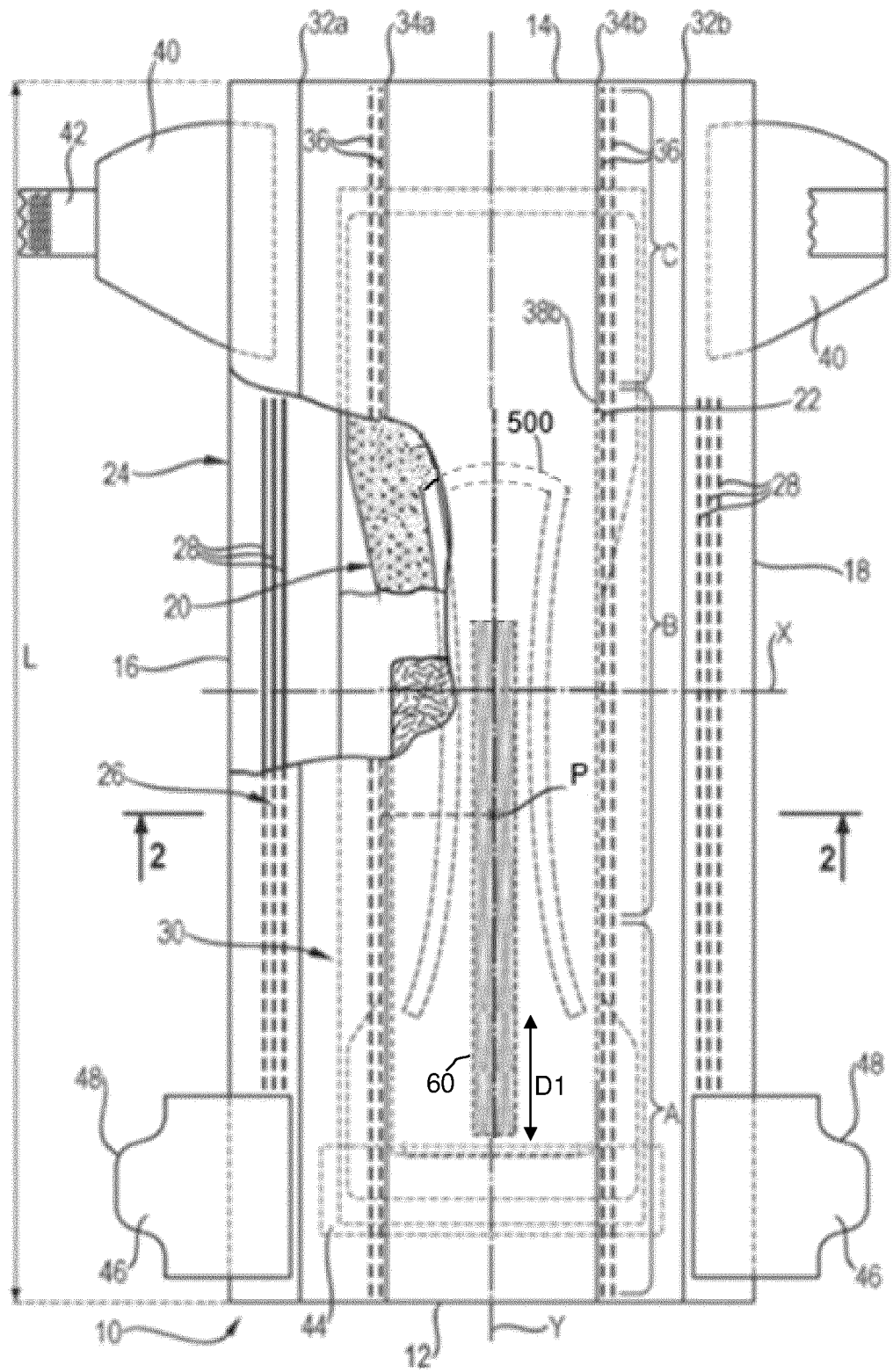
FIG. 19 is a top view of an absorbent article according to an embodiment of the present disclosure in the form of a diaper with some layers partially removed.

Although above embodiments have been described with reference to plural channels as illustrated in FIG. 18, a person skilled in the art will understand that the same embodiments apply to different channel geometries. For example, as shown in FIG. 19, the channel may be in the form of a single channel 500 that has two parallel and opposing longitudinally extending portions and one transversely extending portion connecting said longitudinally extending portions to form a substantially U-shaped channel 500.

Figure 20:
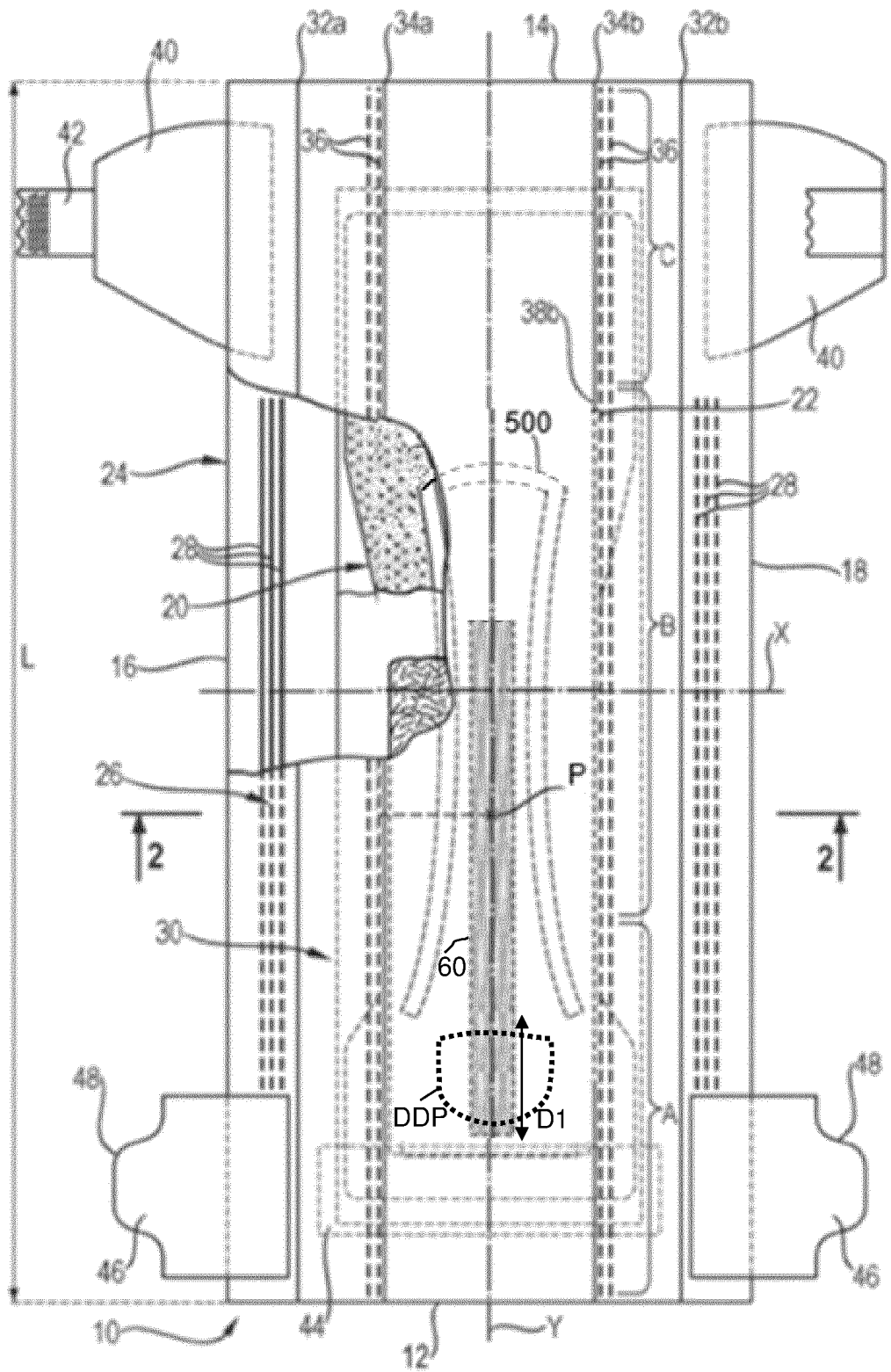
FIG. 20 is a top view of an absorbent article according to an embodiment of the present disclosure in the form of a diaper with some layers partially removed.

In an embodiment, the detection device position DDP is at the front of the absorbent article and overlaps at least a portion of the indicator 60, this is illustrated in FIG. 20. The detection device position DDP may overlap the indicator 60 along an overlap length that is from 60% to 95% of distance D1, preferably from 70% to 90% of distance D1, even more preferably from 75% to 85% of distance D1, and preferably is positioned such that the front-most edge of the indicator 60 remains exposed. Advantageously, allowing the front-most edge of the indicator to remain exposed when the detection device is connected (i.e. 95% or less of D1) ensures limiting risk of interference/noise in the light color detection of the optical sensor (when used as described in embodiments herein below) that may cause false warnings at the same time ensuring sufficient distance from the channels (i.e. 60% or more of D1) allows for reduced risk of false saturation warnings when the diaper core is actually not yet saturated.

FIG. 21 illustrates schematically the absorbent articles herein with channels 500, indicator 60 and detection device position DDP as described herein in both dry and wet conditions.

FIG. 2 is transversal cross-section of the embodiment of FIG. 1 and readily shows other structural elements of the diaper. As shown in this figure, the diaper may comprise an acquisition-distribution system 50. This acquisition-distribution system comprises acquisition layer 52, which first receives liquid, and distribution layer 54 underneath acquisition layer 52.

The absorbent core 20 may comprise a core layer 56. This core layer can comprise particular material, such as super absorbent particles, herein also referred to SAP. Between the core layer 56 and the backsheet 24 the indication means 60 can be arranged. As shown in FIG. 2 the backsheet 24 can comprise and inner backsheet layer 62 (which is oriented towards the core 20) and an outer backsheet layer 64, which is generally oriented towards the garments of a wearer. As shown in FIG. 2, in accordance with this particular embodiment, the indicator 60 can be provided above the inner backsheet layer and below the core wrap, more precisely, below the portion of the core wrap 66 which is oriented towards the backsheet 24.

Figure 3:
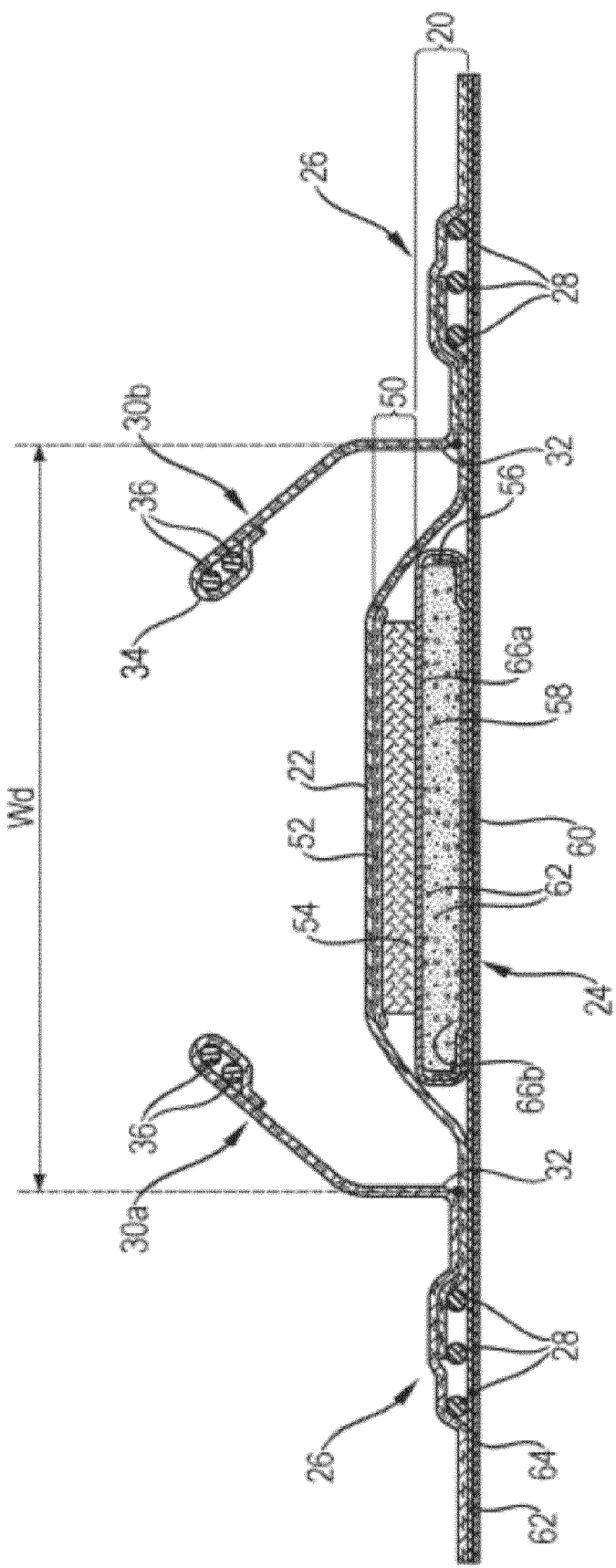
FIG. 3 is a corresponding transversal cross-section of another embodiment of an absorbent article.

FIG. 3 shows another example embodiment of an absorbent article. This embodiment resembles that shown in FIGS. 1 and 2. However, the indicator 60 is arranged here between the inner backsheet layer 62 and the outer backsheet layer 64.

Figure 4:
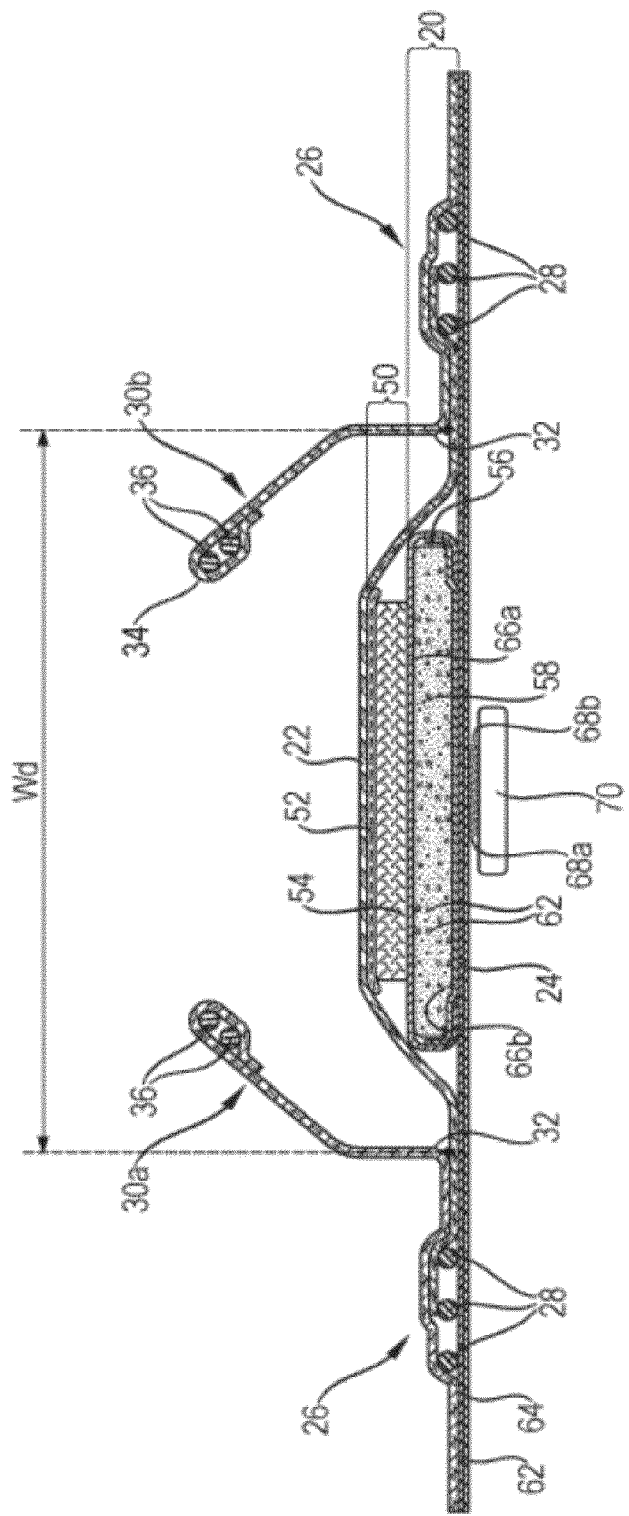
FIG. 4 is a further corresponding transversal cross-section of an embodiment of the present disclosure.

FIG. 4 shows another example embodiment of an absorbent article. For the embodiment shown in FIG. 2 the absorbent article is shown together with detector device 70. As shown, detector device 70 can take the form of a small pod which can have generally rectangular cross sections. The detector device 70 can be attached to the backsheet 24 of the diaper 10 by a mechanical fastener 68. In one embodiment, for example, the mechanical fastener comprises a first component and a second component. The first component can be attached to backsheet 24 and the second component can be attached to detector device 70. The two components interact with each other, for example hook and loop fasteners can be used. The respective component can be adhesively joined to the backsheet and to the detector device 70, respectively.

Alternatively, the detector device may be inserted into or contained within a pocket formed between a garment facing surface of the backsheet and a covering layer, wherein the covering layer typically is a nonwoven comprising a spunbond layer that is joined to the garment facing surface of the backsheet by a joining means, such as adhesive, wherein the joining means is present outboard of the pocket and is absent inboard of the pocket such to form a containment volume for the detector device that may be advantageously retained therein and placed in direct contact with the indicator with no other layers therebetween. This has the advantage to limit light scattering or refraction in cases where a light source and optical sensor are used to measure a change in condition.

The article may also comprise elasticized gasketing cuffs 26 joined to the chassis of the absorbent article, typically via the topsheet and/or backsheet, and substantially planar with the chassis of the diaper.

The Figures also show typical taped diaper components such as a fastening system comprising adhesive tabs 42 attached towards the back edge of the article and cooperating with a landing zone 44 on the front of the article. The absorbent article may also comprise other typical elements, which are not represented, such as a back elastic waist feature, a front elastic waist feature, transverse barrier cuff(s), a lotion application, etc.

The topsheet 22, the backsheet 24, the absorbent core 20 and the other article components may be assembled in a variety of well known configurations, in particular by gluing or heat embossing. Exemplary diaper configurations are described generally in U.S. Pat. Nos. 3,860,003, 5,221,274, 5,554,145, 5,569,234, 5,580,411, and 6,004,306. The absorbent article is preferably thin. The caliper at the crotch point P of the article may be for example from 4.0 mm to 12.0 mm, in particular from 6.0 mm to 10.0 mm, as measured with a suitable caliper test, for example the Absorbent Article Caliper Test disclosed in EP 2 740 450 A1 (Applicant: The Procter & Gamble Company).

These and other components of the articles will now be discussed in more details.

The topsheet 22 is the part of the absorbent article that is directly in contact with the wearer's skin. The topsheet 22 can be joined to the backsheet 24, the core 20 and/or any other layers as is known in the art. Usually, the topsheet 22 and the backsheet 24 are joined directly to each other in some locations (e.g. on or close to the periphery of the article) and are indirectly joined together in other locations by directly joining them to one or more other elements of the diaper 10.

The topsheet 22 is preferably compliant, soft-feeling, and non-irritating to the wearer's skin. Further, at least a portion of the topsheet 22 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or combinations thereof, e.g. a combination of natural and synthetic fibers. A combination of materials can be achieved by combining at least two materials by means of needle punching, ultra-sonic bonding, ring rolling, embossing, gluing or other types of mechanical entanglement. The resulting material may maintain a dual/multiple layer structure, but may also loose a structure of distinguishable layers after such process steps. It can also be useful to provide a formed film patch underneath the topsheet.

If the topsheet 22 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

The topsheet 22 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 mm2 and about 50 mm2, in particular between about 15 mm2 and 35 mm2. Examples of apertured topsheet are disclosed in U.S. Pat. No. 6,632,504, assigned to BBANONWOVENS SIMPSONVILLE. WO2011/163582 also discloses suitable colored topsheet having a basis weight of from 12 to 18 gsm and comprising a plurality of bonded points. Each of the bonded points has a surface area of from 2 mm2 to 5 mm2 and the cumulated surface area of the plurality of bonded points is from 10 to 25% of the total surface area of the topsheet. Typical diaper topsheets have a basis weight of from about 10 to about 21 gsm, in particular between from about 12 to about 18 gsm but other basis weights are possible.

The backsheet 24 is generally that portion of the diaper 10 positioned adjacent the garment-facing surface of the absorbent core 20 and which prevents the exudates absorbed and contained therein from soiling articles such as bedsheets and undergarments. The backsheet 24 is typically impermeable to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 10 while still preventing exudates from passing through the backsheet 24. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 24 may be joined to the topsheet 22, the absorbent core 20 or any other element of the diaper 10 by any attachment means known in the art. Suitable attachment means are described above with respect to means for joining the topsheet 22 to other elements of the diaper 10. For example, the attachment means may include a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core 20 of the absorbent article may comprise a first core layer 56 and a second core layer 58. As explained, the absorbent article might comprise and acquisition distribution system, which will typically consist of one or more layers. Most typically, the layers are arranged above the core layer. Hence, a number of layers can be arranged between the topsheet and the backsheet. The skilled person will usually have no difficulty in distinguishing between these layers. In case of doubt, a core layer can be identified as being a layer which is generally less permeable than a layer forming part of the acquisition-/distribution-system.

Permeability generally refers to the quality of a porous material that causes it to a lower liquid or gases to pass through it. Hence, the layers of the acquisition distribution system should generally be more permeable than the layers of the core system as these layers are meant to distribute liquid to the absorbent core, where the liquid is ultimately stored.

The absorbent core can comprise absorbent material with a varying amount of superabsorbent polymers (herein abbreviated as "SAP"), often enclosed within a core wrap. The SAP content can represent from 0% to 80% by weight of the absorbent material contained in the core wrap. Often an SAP content of 20% to 50% by weight of the absorbent material contained in the core wrap is useful. The core wrap is not considered as absorbent material for the purpose of assessing the percentage of SAP in the absorbent core.

The SAP content may be higher than 30%, for example at least 40%, at least 50%, at least 80% of the weight of the absorbent material contained within the core wrap. The absorbent material may in particular embodiments comprise from 10 to 70, for example 30 to 60 weight percent of natural or synthetic fibers.

The absorbent core may comprise a generally planar top edge and a generally planar bottom edge. In some embodiments, the absorbent material will be advantageously distributed in higher amount towards the front edge than towards the rear edge as more absorbency is required at the front. In other embodiments, typically embodiments for other uses of an absorbent article, such as care of elderly incontinent people versus care of babies, the absorbent material will be advantageously distributed in higher amount towards the rear edge than towards the front edge as more absorbency is required at the rear area.

The core wrap may be formed by two separate sheets of nonwoven material which may be at least partially sealed along the edges of the absorbent core. The core wrap may be at least partially sealed along its front edge, back edge and two longitudinal edges so that substantially no absorbent material leaks out of the absorbent core wrap.

The absorbent core of the absorbent article may further comprise adhesive for example to help immobilizing the SAP within the core wrap and/or to ensure integrity of the core wrap, in particular when the core wrap is made of two or more substrates. Such an adhesive can be provided in the form of fibrous thermoplastic adhesive material.

The fibrous thermoplastic adhesive material may be at least partially in contact with the superabsorbent material in the land areas and at least partially in contact with the substrate layer in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material.

The thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

Superabsorbent material, herein also referred to as superabsorbent polymer material, superabsorbent polymers or SAP, refers to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may in particular have a CRC value of more than 20 g/g, or more than 24 g/g, or of from 20 to 50 g/g, or from 20 to 40 g/g, or 24 to 30 g/g. The SAP useful in example absorbent articles may include a variety of water-insoluble, but water-swellable polymers capable of absorbing large quantities of fluids.

The superabsorbent polymer can be in particulate form so as to be flowable in the dry state. Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked.

The SAP useful for example embodiments of absorbent articles may be of numerous shapes. The term "particles" refers to granules, fibers, flakes, spheres, powders, platelets and other shapes and forms known to persons skilled in the art of superabsorbent polymer particles. In some embodiments, the SAP particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 µm, and preferably less than 250 µm down to 50 µm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 to 850 µm, preferably from 100 to 710 µm, more preferably from 150 to 650 µm, as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 µm to 4000 µm, more specifically a particle size distribution within the range of from 45 µm to about 2000 µm, or from about 100 µm to about 1000, 850 or 600 µm. The particle size distribution of a material in particulate form can be determined as it is known in the art, for example by means of dry sieve analysis (EDANA 420.02 "Particle Size distribution).

The total amount of SAP present in the absorbent core may also vary according to expected usage. Diapers for newborns may require less SAP than infant or adult incontinence diapers. The amount of SAP in the core may be for example comprised from about 2 to 60 g, in particular from 5 to 50 g or 10 to 40 g. The average SAP basis weight within the (or "at least one", if several are present) deposition area of the SAP may be for example of at least 50, 100, 200, 300, 400, 500 or more g/m2. The areas of the channels present in the absorbent material deposition area, if any, are deduced from the absorbent material deposition area to calculate this average basis weight.

The optional core wrap may be made of a single substrate folded around the absorbent material, or may advantageously comprise two (or more) substrates which are attached to another. Typical attachments are the so-called C-wrap and/or sandwich wrap. In a C-wrap, as exemplarily shown in FIG. 2, the longitudinal and/or transversal edges of one of the substrate are folded over the other substrate to form flaps. These flaps are then bonded to the external surface of the other substrate, typically by gluing.

If the core wrap comprises a first substrate 66a and a second substrate 66b these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. It is advantageous that the top side of the core wrap, i.e. the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles.

The absorbent article may comprise a pair of barrier leg cuffs 30. The barrier leg cuffs can be formed from a piece of material, typically a nonwoven, which is partially bonded to the rest of the article so that a portion of the material, the barrier leg cuffs, can be partially raised away and stand up from the plane defined by the topsheet when the article is pulled flat as shown e.g. in FIG. 1. The barrier leg cuffs can provide improved containment of liquids and other bodily exudates approximately at the junction of the torso and legs of the wearer. The barrier leg cuffs extend at least partially between the front edge and the back edge of the diaper on opposite sides of the longitudinal axis and are at least present at the level of the crotch point (P). The barrier leg cuffs are delimited by a proximal edge 32 joined to the rest of the article, typically the topsheet and/or the backsheet, and a free terminal edge 66, which is intended to contact and form a seal with the wearer's skin. The barrier leg cuffs are joined at the proximal edge 32 with the chassis of the article by a bond 33 which may be made for example by gluing, fusion bonding or combination of known bonding means. The bond 33 at the proximal edge 32 may be continuous or intermittent. The side of the bond 33 closest to the raised section of the leg cuffs delimits the proximal edge 32 of the standing up section of the leg cuffs. The distance between the inner sides of these bond 33 define the dry and wet width of the article at this level for the purpose of RCWR test (see below).

The barrier leg cuffs can be integral with the topsheet or the backsheet, or more typically be formed from a separate material joined to the rest of the article. Typically the material of the barrier leg cuffs may extend through the whole length of the diapers but is "tack bonded" to the topsheet towards the front edge and back edge of the article so that in these sections the barrier leg cuff material remains flush with the topsheet. Each barrier leg cuff 30 may comprise one, two or more elastic 36 close to this free distal edge 34 to provide a better seal.

In addition to the barrier leg cuffs 30, the article may comprise gasketing cuffs 26, which are joined to the chassis of the absorbent, article, in particular the topsheet and/or the backsheet and are placed transversely outwardly relative to the barrier leg cuffs. The gasketing cuffs can provide a better seal around the thighs of the wearer. Usually each gasketing leg cuff will comprise one or more elastic string or elastic element comprised in the chassis of the diaper for example between the topsheet and backsheet in the area of the leg openings.

Embodiments of the absorbent articles may comprise an acquisition-distribution layer or system 50 (herein "ADL") and may be a single layer (preferably a spunbond or carded thermobonded layer, or an air-layed nonwoven layer) or may be multilayer and comprising one or more of the following nonwoven layers: spunbond, carded thermobonded, melt-blown, and combinations thereof. The function of the ADL is to quickly acquire the fluid and distribute it to the absorbent core in an efficient manner. The ADL may comprise one, two or more layers, which may form a unitary layer or remain discrete layers which may be attached to each other. In the examples below, the ADL can comprise two layers: a distribution layer 54 and an acquisition layer 52 disposed between the absorbent core and the topsheet, but embodiments of absorbent articles are not restricted to this example and rather multilayer or single-layer ADLs are equally contemplated herein.

Typically, the ADL will not comprise SAP as this may slow the acquisition and distribution of the fluid.

The distribution layer 54 and the acquisition layer 52 may comprise the same or different layers.

For example the distribution layer 54 may be a nonwoven selected from a spunbond, meltblown, carded (preferably thermobonded), and combinations thereof.

The ADL may comprise an acquisition layer 52. The acquisition layer may be disposed between the distribution layer 54 and topsheet 22. The acquisition layer 52 may typically be or comprise a non-woven material, for example a SMS or SMMS material, comprising a spunbonded, a melt-blown and a further spunbonded layer or alternatively a carded chemical-bonded nonwoven.

The absorbent article may include a fastening system. The fastening system can be used to provide lateral tensions about the circumference of the absorbent article to hold the absorbent article on the wearer as is typical for taped diapers. This fastening system is not necessary for training pant article since the waist region of these articles is already bonded. The fastening system usually comprises a fastener such as tape tabs (also referred to as adhesive tabs), hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached.

The absorbent article may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing or pressure bonding. The back ears 40 are advantageously stretchable to facilitate the attachment of the adhesive tabs 42 on the landing zone 44 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

The absorbent article may also comprise at least one elastic waist feature that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 20 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Typically, adjacent layers and components will be joined together using conventional bonding method such as adhesive coating via slot coating or spraying on the whole or part of the surface of the layer, or thermo-bonding, or pressure bonding or combinations thereof. This bonding is not represented in the Figures (except for the bonding by bonds 33 between the raised elements of the barrier leg cuffs 30 with the topsheet 22) for clarity and readability but bonding between the layers of the article should be considered to be present unless specifically excluded. Adhesives may be typically used to improve the adhesion of the different layers, for example between the backsheet and the core wrap. The glue may be any standard hotmelt glue as known in the art.

Figure 5:
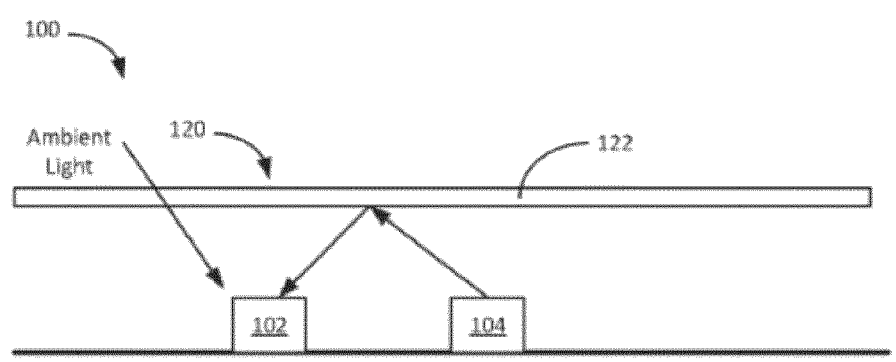
FIG. 5 shows a partial schematic view of an example embodiment of a reusable detector device that may be removably attached externally to a diaper, such as shown in FIG. 4

FIGS. 5A and 5B show partial schematic views of an example embodiment of a reusable detector device 100 that may be removably attached externally to a diaper, such as shown in FIG. 4. In this example embodiment, for example, all electronic components of the detector may be disposed outside the diaper. The detector device 100 is adapted to detect one or more color changes in an indicator 120, such as a color change strip 122, disposed within the diaper. In this particular embodiment, the indicator 120 changes color directly or indirectly in response to presence and/or absence of a bodily exudate within the diaper.

The color change strip 122, for example, may be disposed in the diaper such as shown in FIG. 1 generally along a mid-line of the diaper and extend a predetermined distance in the cross-direction of the diaper. In one particular embodiment, for example, the color change strip 122 is between approximately 4 mm and 45 mm wide, preferably from 10 mm to 40 mm wide, even more preferably from 12 mm to 35 mm wide, even more preferably from 15 mm to 30 mm wide, such as approximately 20 mm wide, and between approximately 100 and 300 mm long, such as approximately 100 mm, 150 mm, 200 mm, 250 mm or 300 mm long. The dimensions of the color change strip, however, are merely exemplary and not limiting. The color change strip 122 (or other indicator 120), for example, may include any number of form factors, such as but not limited to one or more stripes, circles, rectangles, dots, designs (e.g., a character or other drawing). The indicator 120 may also be disposed in other locations of the diaper than shown in FIG. 1. Further, where the indicator 120 includes a material (e.g., adhesive, SAP/AGM) that migrates within the diaper or fades as the more bodily exudates are introduced into the diaper, a detection algorithm may maintain a state of wet/soiled once an initial detection has been made. For example, a ratchet or other feature in an algorithm may be used to maintain an indication that bodily exudates have been detected until the diaper has been changed or the detector 100 has been removed from the diaper.

The detector device 100 includes one or more optical (e.g., color) sensors 102 and a light source 104 (e.g., an LED). The optical sensor 102 measures one or more light levels from the indicator 120. In one particular embodiment, for example, the color sensor measures four light levels—clear, red, green and blue—with a sixteen (16) bit resolution. The clear level corresponds to a measure of an overall light intensity and the red, green and blue levels correspond to intensity in the relevant parts of the spectrum from the indicator 120. In this embodiment, the detector device 100 takes multiple measurements with the optical sensor 102. In a first operation, the optical sensor 102 is read without the light source 104 (e.g., the LED) illuminated to determine a background light level. Another reading of the color sensor is taken in another operation with the light source 104 illuminating the color change strip 122 of the indicator 120 to measure the clear, red, green and blue (RGB) light levels. A difference between the two measurements is obtained in a third operation and represents a color of the color change strip 122 of the indicator 120. The clear color level may be used to normalize the RGB values. Fill levels corresponding to one or more intermediate states of the indicator 120 may also be determined, such as from the hue, saturation and brightness (HSB) values in combination with or instead of the RGB values.

The optical sensor 102 may be spaced (or be positioned distal) from the light source 104 so that direct light from the light source 104 is reduced or eliminated at the optical sensor 102. Similarly, too large a spacing between the optical sensor 102 and the light source 104 may reduce the signal strength at the optical sensor 102. In one embodiment, for example, the optical sensor 102 may be spaced at least about 5 mm from the light source 104. In another embodiment, the optical sensor may be spaced at least about 8 mm from the light source 104, at least about 10 mm from the light source 104, between approximately 5 and 20 mm from the light source 104, and between approximately 10 to 15 mm from the light source 104.

In one embodiment, the optical sensor 102 may be positioned substantially between a plurality of light source 104. For example, when two light sources are used, they are spaced apart along an axis and the optical sensor is positioned about mid-way along said axis. Alternatively, in case more than two light sources are used, they are preferably positioned along a circumference of an imaginary circle and the optical sensor is positioned at about the centre of said imaginary circle.

In addition to spacing between the optical sensor 102 and the light source 104, other factors may also affect light level measurements of the optical sensor 102. For example, temperature, location of the detector device 100 on the diaper, the type, material and color of a connector (e.g., adhesive, tape, hook and loop, strap and other materials) disposed between the detector device 100 and the indicator 120 disposed within the diaper, orientation of the detector device 100 relative to the indicator 120, orientation of transmit and receive windows of the detector device 100 and the diaper, force of application of the detector device 100 against the diaper (e.g., may affect the distance between the optical sensor 102 and light source 104 of the detector device 100 and the indicator 120 of the diaper in use), ambient light, placement of an attachment zone on the diaper for coupling to the detector device 100 and placement of the detector device 100 relative to the indicator 120 of the diaper (e.g., in a cross-direction) such that the optical sensor 102 detects other components of the diaper disposed near the indicator 120.

In one embodiment, for example, the color change strip 122 changes color in response to a change in pH within the diaper. Swelling of Super Absorbent Polymers (SAP)/Absorbent Gelling Materials (AGM) within the diaper changes the pH of the environment within the diaper. In response to a change in pH, the color change strip 122 changes in color. The color change strip 122, for example, may comprise a pH sensitive glue, such as H9588 glue that is commercially available from Bostik. While a human eye may only be able to distinguish general changes in color, such as a transition from yellow (dry) to blue (wet), an electronic color sensor such as a photodiode can detect intermediate colors as the indicator transitions from a first state to a second state.

Although a pH sensitive color change strip 122 is discussed with respect to an example embodiment, the indicator 120 is not so limited. Rather, the indicator 120 may include any indicator that changes color or other appearance directly or indirectly related to the presence or absence of bodily exudates within the diaper. For example, color change materials that change from no color to one or more colors, from one or more colors to no colors, change colors in other color ranges than the pH sensitive adhesive described herein, materials that change color or appearance based on factors other than pH changes, such as but not limited to, temperature, wetness, odor, enzymes, organic components, inorganic components (e.g., salt level), colored SAP/AGM, mechanical forces (e.g., strain, stretch) or the like.

Preferred however, are indicators that change from yellow (in dry state) to blue (in wet state), and green in a transition state from yellow to blue (or from dry to wet).

As discussed with respect to FIG. 4 above, the detector device 100, may include one or more user signal devices, which may include an audio and/or visual indicator such as but not limited to one or more LEDs, LCDs, display screens, lights, speakers or other indicators, that may be used to indicate the presence and/or absence of bodily exudates detected within the diaper.

The detector device 100 may further include a communication module 106 adapted to transmit data from the detector device 100 to a remote device 130, such as for storage and/or presentation to a user. The communication module 106, for example, may include a Bluetooth communication module, a BTLE communication module, a mesh communication module (e.g., IEEE 802.15.4), a WiFi communication module (e.g., IEEE 802.15.11), a communication module incorporating all or any portion of IEEE 802 or similar communication standards, an RFID module, a 3G or 4G communication module, a Backscatter communication module, a light communication module, a sound communication module, a harvesting protocol communication module (e.g., a metadata harvesting protocol communication module. Other communications protocols or combinations of communications protocols (e.g., a Bluetooth/Mesh combined protocol) and mechanisms may also be used.

In one embodiment, for example, a smartphone, tablet, computer or other remote device may be used to receive information from the detector device 100, determine one or more state of the diaper (e.g., presence or absence of one or more bodily exudates) and display information related to the state of the diaper to a user. The remote device may be in direct communication with the detector device and/or be communicatively coupled with detector device (or via an intermediate device) via one or more computer networks, such as the Internet.

Figure 6:
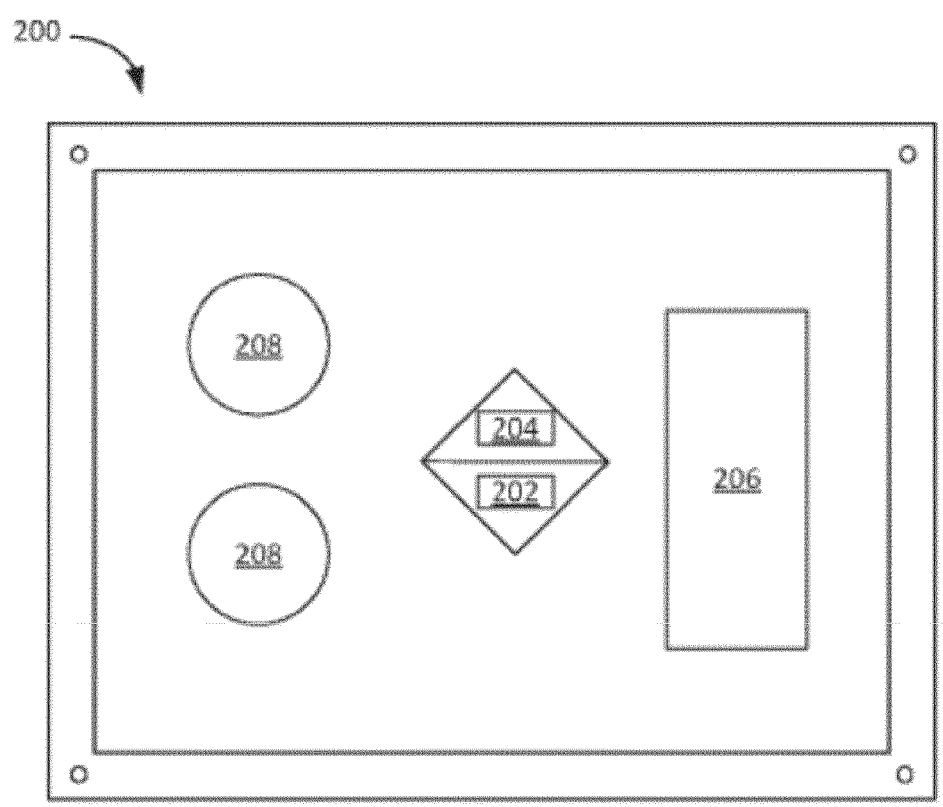
FIG. 6 shows a block diagram of an example implementation of a detector device adapted for removably coupling with one or more diapers.

FIG. 6 shows a block diagram of an example implementation of a detector device 200 adapted for removably coupling with one or more diapers. In this particular embodiment, the detector device 200 includes a color sensor 202, an LED light source 204, a low energy Bluetooth (BTLE) communication module 206 and one or more batteries 208. The batteries 208, for example, may include one or more silver oxide batteries, nickel cadmium batteries, lithium batteries, alkaline batteries, capacitors or other energy storage devices. The batteries 208 may be disposable or rechargeable and provide power to the other components of the detector device 200.

In one embodiment, the detector device may further include one or more processors and memory storage for providing processing on the detector device 200.

The communications module 206, for example, may be limited in power and/or duration of transmission to reduce electromagnetic (EM) energy transmitted in close proximity to a wearer of the diaper. The BTLE module 206, for example, may be operated at approximately 2 mW for approximately 0.005% time of the time it is in operation (approximately one transmission per minute).

Figure 7:
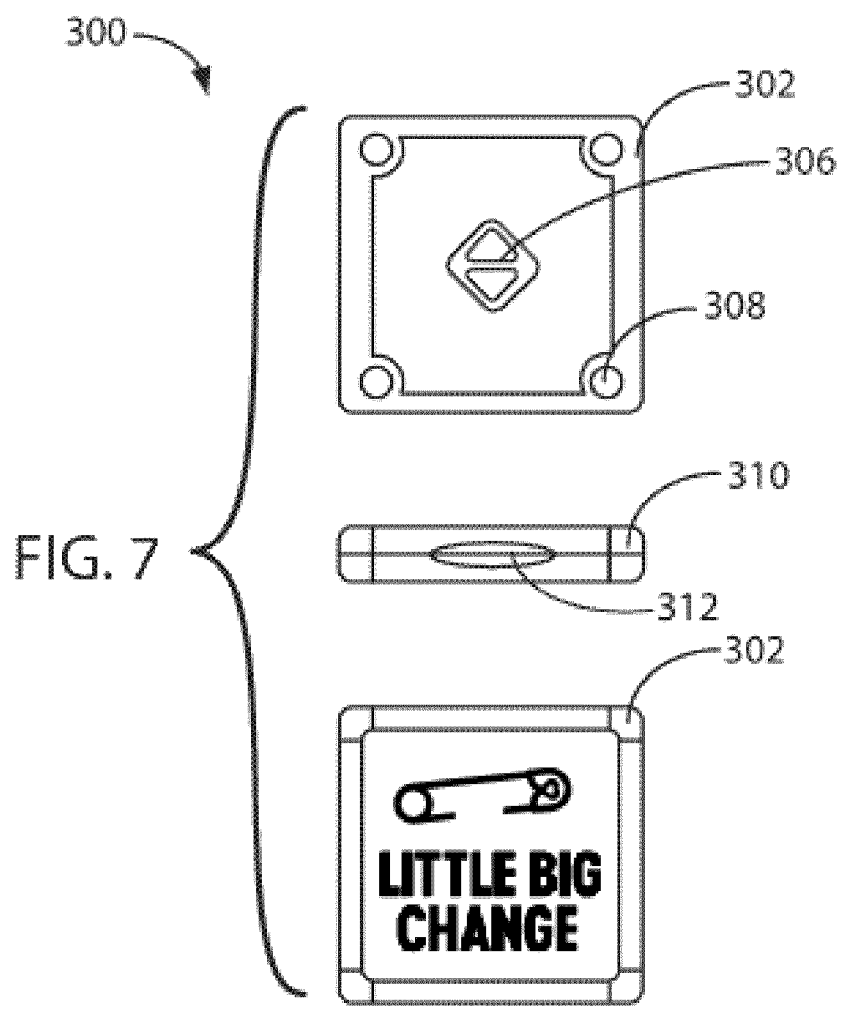
FIG. 7 shows top, bottom and side views of an example embodiment of an exterior of a detector device, such as the one shown in FIG. 6.
Figure 8:
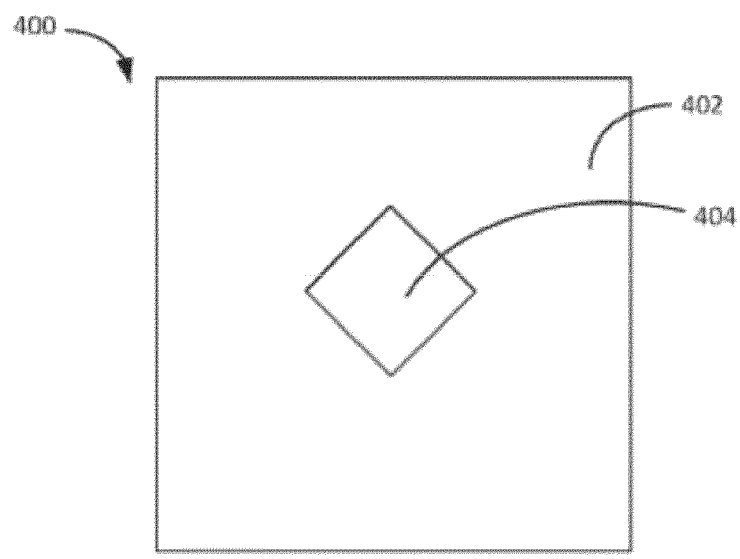
FIG. 8 shows an example embodiment an attachment zone of a diaper exterior adapted for receiving a detector device, such as the detector device shown in FIGS. 6-7.

FIG. 7 shows top, bottom and side views of an example embodiment of an exterior of a detector device 300, such as the one shown in FIG. 8. In this embodiment, the top side 302 of the device 300 faces outwardly from a diaper in use and includes a decorative design. The bottom side 304 of the device includes a window 306 through which a light source, such as the LED light source 204 shown in FIG. 6, may transmit to an indicator disposed within the diaper and a color sensor may detect one or more colors of the indicator. In the particular embodiment shown in FIG. 7, for example, the a plurality of screws 308 or other connectors may secure the top and bottom components to each other. The side 310 includes a notch 312 or other opening to assist a user to separate the top and bottom sides 302, 304 if the screws 308 are disengaged.

The container of the detector device 300 maybe sized and shaped to prevent the device 300 from being a choking hazard. The container may further include materials such as silicone, Tecaform, Tecanat or other materials. The device container may also include one or more muted colors to minimize its attractiveness to children.

FIG. 8 shows an example embodiment an attachment zone 400 of a diaper exterior adapted for receiving a detector device, such as the detector device shown in FIGS. 6 and 7. The attachment zone 400 includes a landing zone material 402 to improve attachment of the detector device to the diaper. The landing zone material 402, for example, may include a brushknit or adhesive or cohesive tape material for mechanically or adhesively coupling the detector device to an outer surface of the diaper. The landing zone material 402 includes a window opening 404 that corresponds to the window of the detector device (e.g., window 306 shown in FIG. 7). In one particular implementation, the landing zone material 402 may be sized and shaped similarly to the detector device so as to facilitate placement of the detector device on the outer surface of the diaper. Other landing zone materials are also contemplated. For example, loop, hook, adhesive, strap, button, snap, pocket, magnet, or other materials may be used on the diaper and/or detector device.

Alternatively, a pocket design such as described on paragraphs 0079-0084, 0128 and 0130-0131 of EP3451988 herein incorporated by reference. Advantageously, by being retained is such pocket the risk of accidentally decoupling the clip-on unit is limited.

Figure 9:
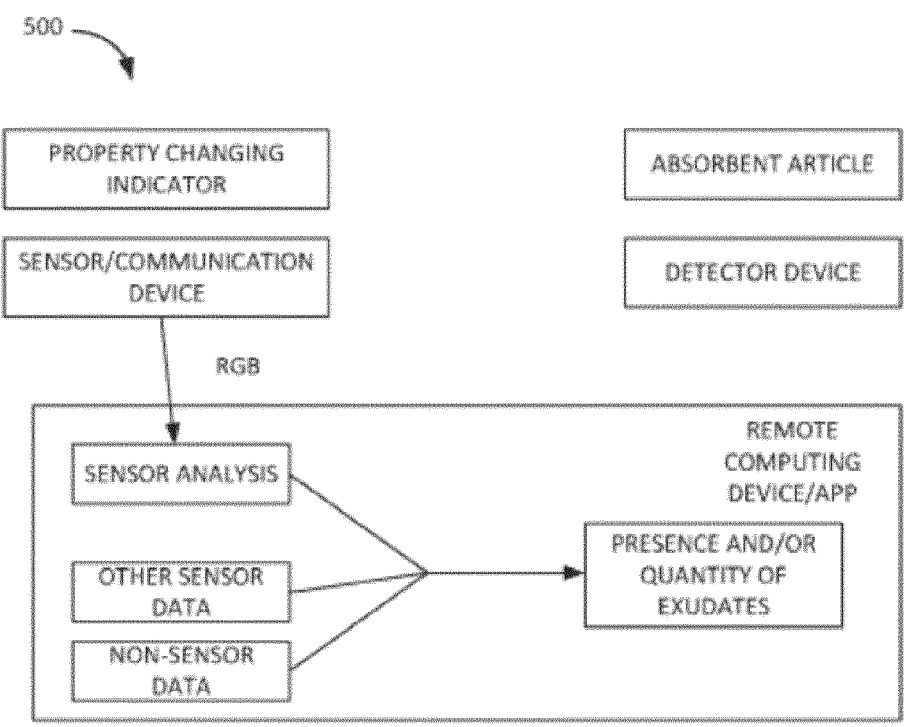
FIG. 9 shows a flow diagram of example operations that may be used to detect one or more bodily exudates within a diaper.

FIG. 9 shows a flow diagram of example operations that may be used to detect one or more bodily exudates within a diaper. In this embodiment, a detector device includes one or more color sensors for detecting one or more state of an indicator in a diaper. As described above, a color sensor of the detector device may determine one or more RGB light levels or HSB levels of the indicator. A communications device of the detector device may provide information based upon a detected color of the indicator to a remote computing device. The remote computing device then predicts presence, absence and/or amount of one or more bodily exudates based at least in part on the information received from the detector device. The remote computing device, for example, may determine a local saturation (e.g., exudate content quantity) level based upon the information received from the detector device.

The remote computing device may further receive additional inputs, such as but not limited to, weartime, the time the absorbent article was attached to a wearer, the current time, absorbent article user information (e.g., baby demographic information such as sex, age, weight of wearer, whether the wearer is toilet training, degree of wearer incontinence), user input information, caregiver preference information, biometric information of the wearer, ambient sensor information and/or contextual information, and may use these additional inputs separately and/or in combination with the information received from the detector device.

In the particular embodiment, shown in FIG. 9, for example, the remote computing device determines a predicted diaper fullness level (e.g., an exudate content quantity of the absorbent article such as a liquid and/or solid exudate content quantity) or state based at least in part upon the sensor information received from the detector device and contextual information (e.g., wear time of the diaper and baby demographic information). Contextual information, for example, may be input by consumers, retrieved via other sensors or information sources (e.g., thermostats). Sensor data, for example, may include property change indications (e.g., digital or analog such as an intensity of color change in a color changing indicator) and wear time. In one implementation, an analog detection may be based upon a calibration of an indicator (e.g., color) for different exudate loADL. Wear time, for example, may be described as the time determined between attachments of two fresh diapers.

Further, in one example, exudate fullness may be determined by the following functions:

Urine Fullness=f (Property Change Detection, wear time, wearer data and other data)

Property Change Detection=f (color sensor data).

An exudate content quantity, for example, may be provided to a user to indicate a percent or other indication of diaper fullness or remaining capacity on the detector device, a remote display or a remote computing device. In one particular implementation, for example, the remote display or computing device may display a graphical or numerical representation of exudate content quantity or remaining capacity of the absorbent article.

Calibration of the color of the indicator to a particular exudate load quantity, for example, can be determined in a number of manners. For example, in one embodiment, different load quantities of an absorbent article may be introduced and corresponding colors can then be measured. In another embodiment, for a given load quantity, a color change may be mapped versus time measured during loading to provide a kinetic curve that represents an exudate load quantity versus time.

Figure 10:
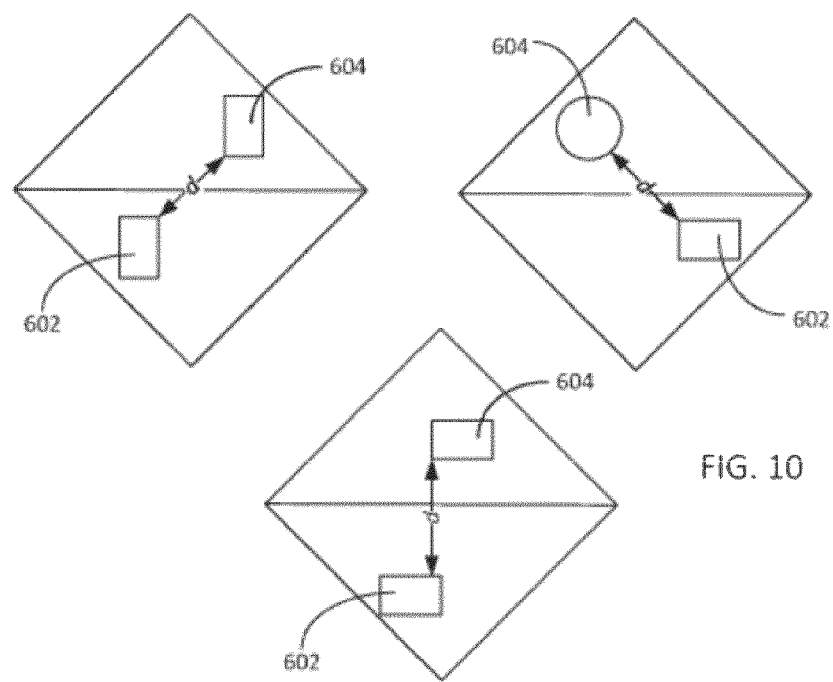
FIG. 10 shows example embodiments of spaced optical sensor and light element 604 pairs of example embodiments of one or more detector devices.

FIG. 10 shows example embodiments of spaced optical sensor 602 and light element 604 pairs of example embodiments of one or more detector devices. In these embodiment, various combinations of sensors (e.g., optical and/or color sensors) are spaced by a distance d from each other. For purposes of the present disclosure, the measurement d is a straight line measurement from the nearest points of the various optical sensors 602 and light elements 604. In one example embodiment, for example, the optical sensor 602 and light element 604 are spaced at least about 5 mm from each other. In other embodiments, the optical sensor 602 and light element 604 are spaced at least about 8 mm, at least about 10 mm, between about 10 mm and about 15 mm and between about 10 mm and 20 mm.

Figure 11:
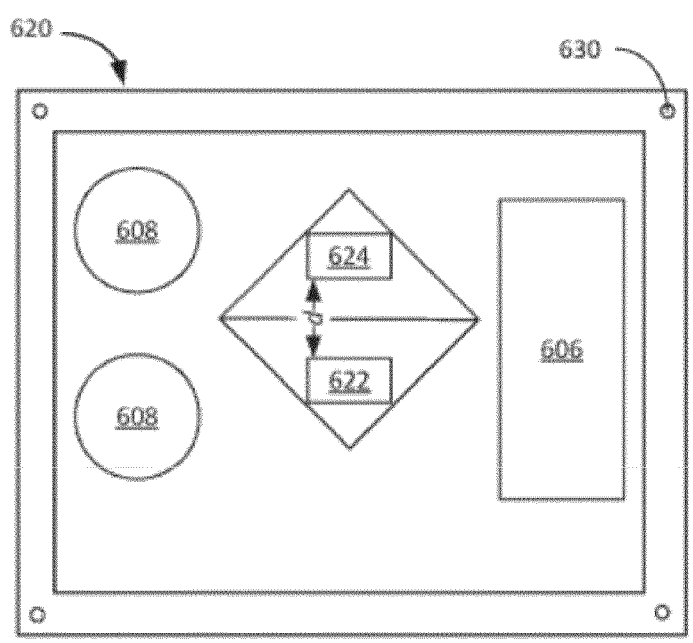
FIG. 11 shows another example embodiment of a detector device. In this embodiment, for example, an optical sensor and a light element are spaced from each other.

FIG. 11 shows another example embodiment of a detector device 620. In this embodiment, for example, an optical sensor 622 and a light element 624 are spaced from each other a distance d. The detector device 620 further includes a communication module 606 and a pair of batteries 608. Screw holes 630 are also provided to allow a cover to be securely fastened to enclose the components of the detector device. As described above, the detector device 620 may further include a window opposing the spaced optical sensor 622 and light element 624.

Figure 12:
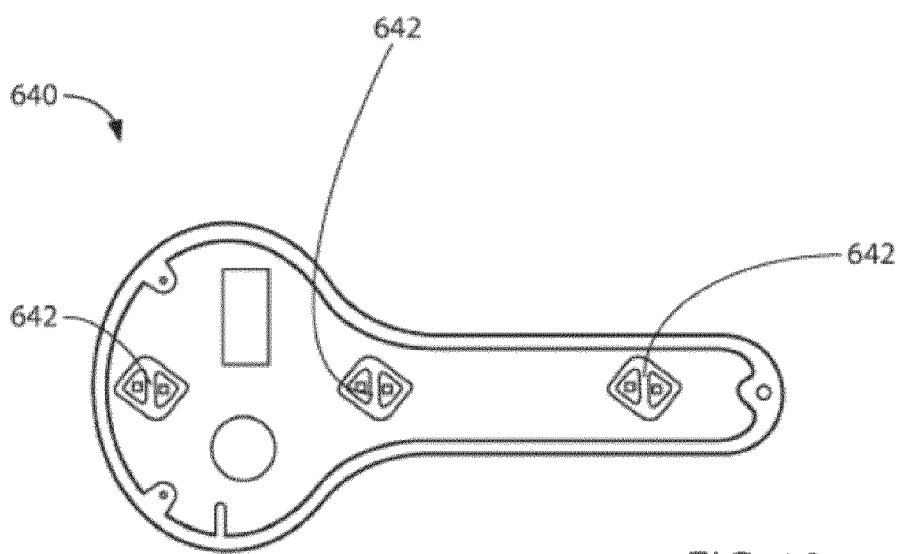
FIG. 12 shows another example embodiment of a detector device comprising a plurality of spaced optical sensor and light pairs.

FIG. 12 shows another example embodiment of a detector device 640 comprising a plurality of spaced optical sensor and light pairs 642. In this particular embodiment, three pairs of individual spaced optical sensor and light pairs 642 are disposed in different locations of the detector device 640 and adapted to detect a change in one or more optical properties at different locations of an absorbent article. The detector device 640 further comprises a communication module 646 and a battery 648 adapted to provide power to the sensors, lights and communication module 646.

Figure 13:
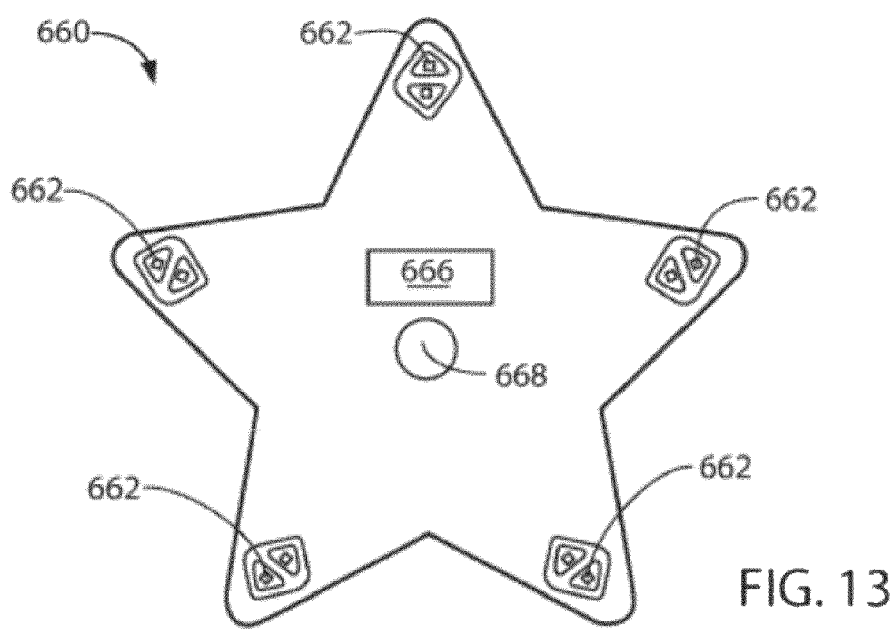
FIG. 13 shows yet another example embodiment of a detector device comprising a plurality of spaced optical sensor and light pairs.

FIG. 13 shows yet another example embodiment of a detector device 660 comprising a plurality of spaced optical sensor and light pairs 662. In this particular embodiment, five pairs of individual spaced optical sensor and light pairs 662 are disposed in different locations of the detector device 660 and adapted to detect a change in one or more optical properties at different locations of an absorbent article. The detector device 660 further comprises a communication module 646 and a battery 668 adapted to provide power to the sensors, lights and communication module 646.

Figure 14:
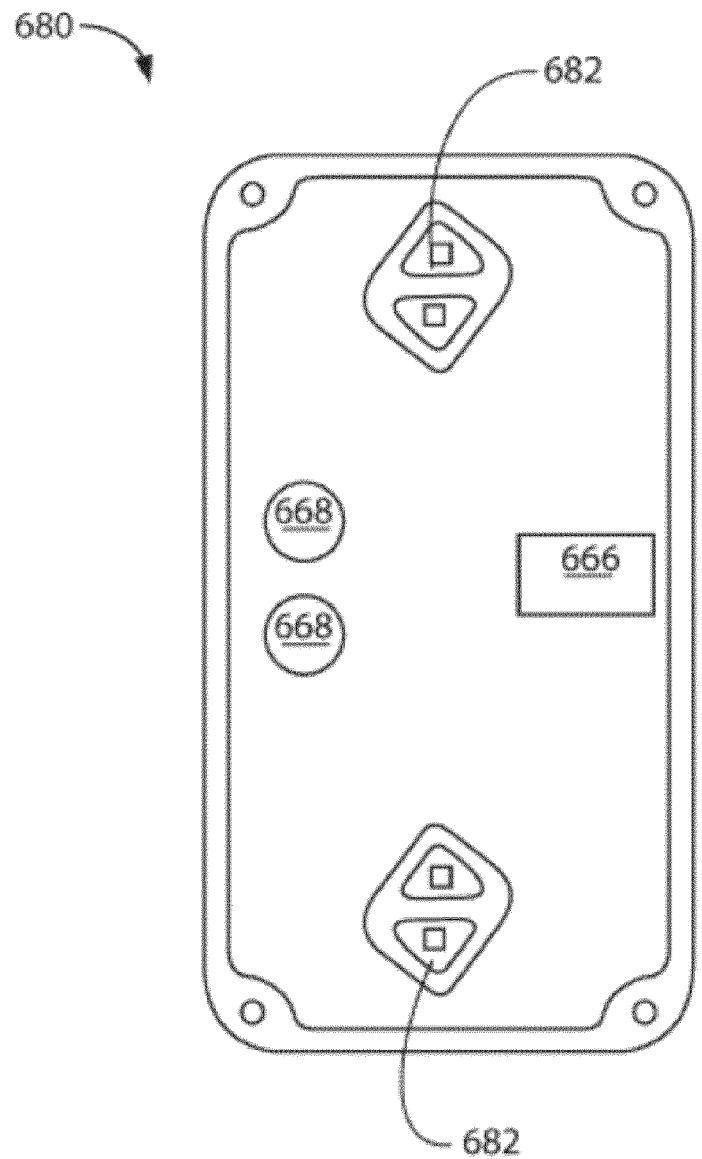
FIG. 14 shows still another example embodiment of a detector devise comprising a plurality of spaced optical sensor and light pairs.

FIG. 14 shows still another example embodiment of a detector device 680 comprising a plurality of spaced optical sensor and light pairs 682. In this particular embodiment, two pairs of individual spaced optical sensor and light pairs 682 are disposed in different locations of the detector device 680 and adapted to detect a change in one or more optical properties at different locations of an absorbent article. The detector device 680 further comprises a communication module 686 and a battery 688 adapted to provide power to the sensors, lights and communication module 686.

Figure 15:
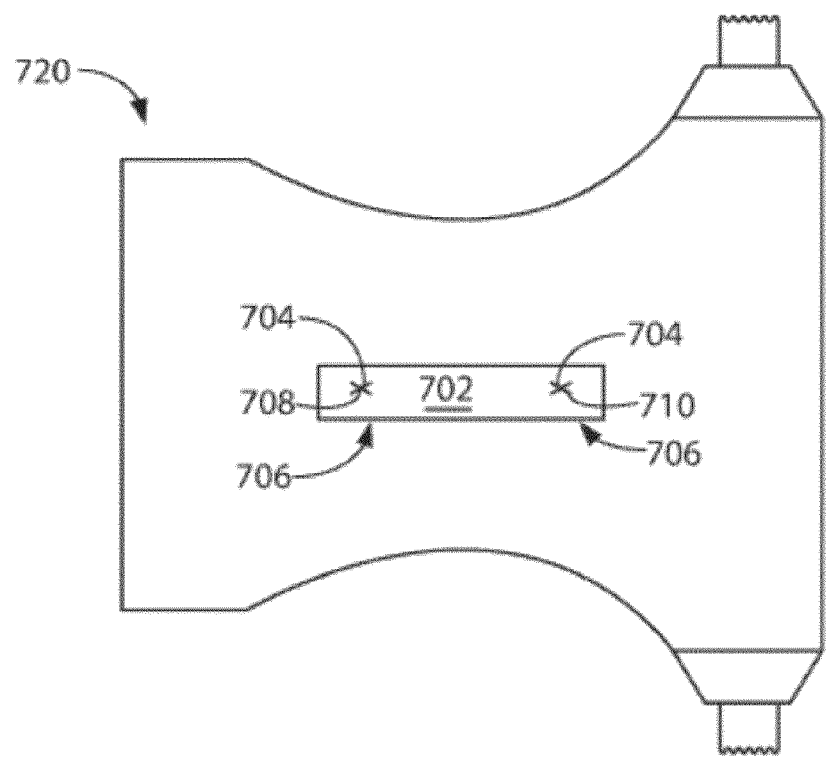
FIG. 15 shows an example embodiment of an absorbent article including a detector device coupled to the absorbent article.

FIG. 15 shows an example embodiment of an absorbent article 700 including a detector device 702 disposed adjacent to the absorbent article 700. In this particular embodiment, the detector device comprises a plurality of sensors 704. Each of the plurality of sensors 704 is spaced from each other and adapted to be disposed opposite different locations 706 of the absorbent article 700. As shown in FIG. 15, for example, a first sensor 708 is disposed opposite a front region of the absorbent article 700 and a second sensor 710 is disposed opposite a crotch region of the absorbent article 700. The first and second sensors 708, 710, for example, may be spaced at least about 2 cm from each other, at least about 3 cm from each other, at least about 4 cm from each other, at least about 5 cm from each other, or at least about 10 cm from each other. This allows the sensors to detect property changes (e.g., optical/color property changes) in different regions of the absorbent article 700. Further, the plurality of sensors 704 may comprise the same or different types of sensors.

By measuring changes in multiple areas of the absorbent article, the detector device may be able to provide a better prediction of the presence and/or quantity of bodily exudates within the absorbent article given the broad distribution of urination patterns, urination loADL, dietary habits, wearer movement and activity during wear time, wearer body dimensions and the like, all of which may have an effect on exudate distribution within the absorbent article.

Figure 16:
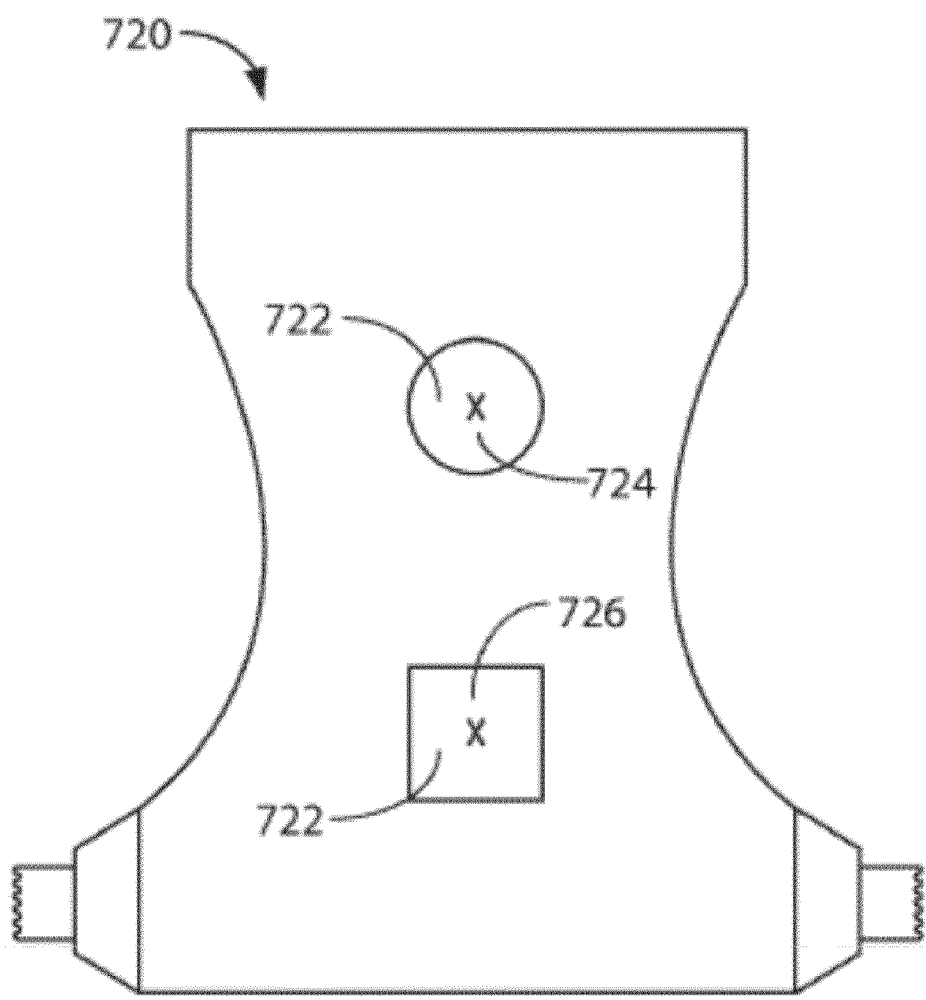
FIG. 16 shows another example embodiment of an absorbent article including a plurality of property changing indicators disposed within the absorbent article.

FIG. 16 shows another example embodiment of an absorbent article 720 including a plurality of property changing indicators 722 disposed within the absorbent article 720. In this embodiment, for example, the plurality of property changing indicators 722 comprises at least a first property changing indicator 724 of a first type and a second property changing indicator 726 of a second type that is different from the first type.

Figure 17:
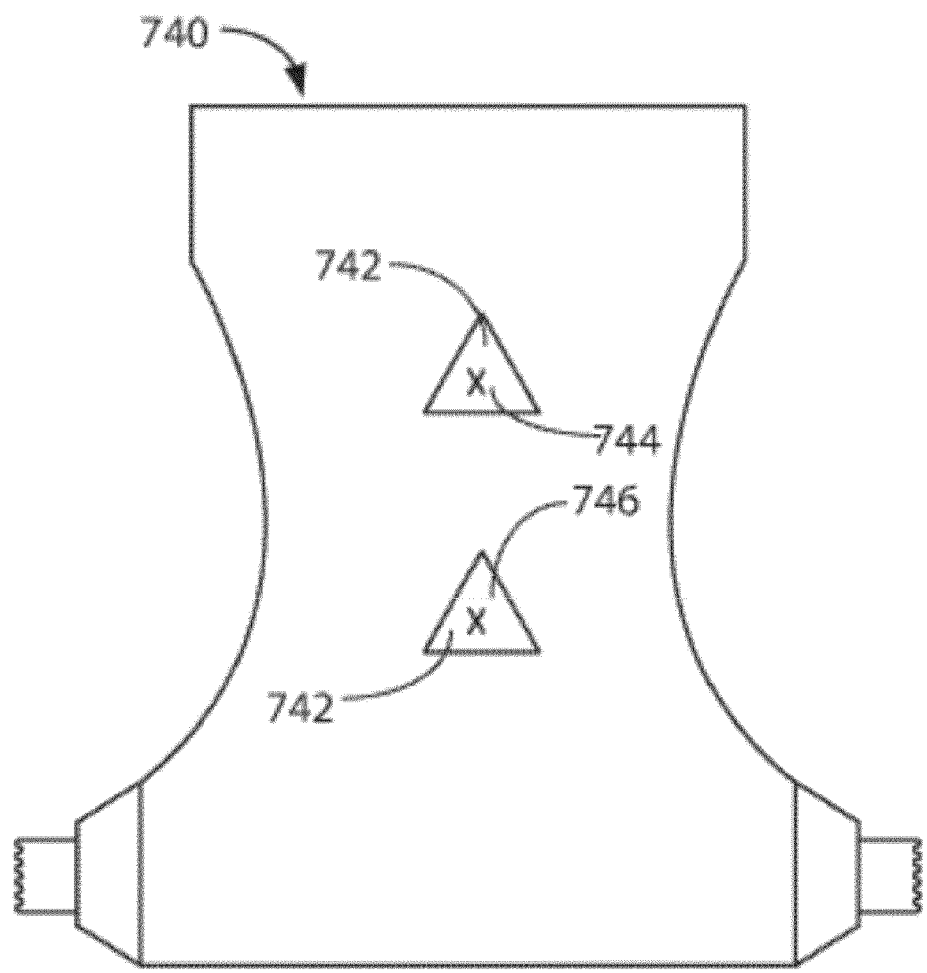
FIG. 17 shows yet another example embodiment of an absorbent article including a plurality of property changing indicators disposed within the absorbent article.

FIG. 17 shows yet another example embodiment of an absorbent article 740 including a plurality of property changing indicators 742 disposed within the absorbent article 740. In this embodiment, for example, the plurality of property changing indicators 742 comprises at least a first property changing indicator 724 and a second property changing indicator 726 of the same type of property changing indicator.

In addition to the sensors described herein adapted to detect one or more property changes of an indicator, the detector devices may further include one or more additional sensors adapted to detect other conditions unrelated to the specific indicators of an absorbent article. For example, the detector device may further include one or more additional sensors such as, but not limited to, a temperature sensor, a humidity sensor, a relative humidity sensor, a chemical sensor, an audio sensor, a microphone, a strain gauge, a material expansion sensor and a vibration sensor.

In an embodiment, a kit comprising an absorbent article and a detection device (70) such as described herein, may comprise a plurality of the absorbent articles and a detection device (70), wherein the detection device (70) is removably attached to the absorbent articles, one after another as they are used, and wherein the detection device (70) is arranged to stop working after a predetermined period of time, preferably wherein the predetermined period of time is more than 20 days and less than 50 days, more preferably from 30 days to 40 days. This allows for combining the sale of such kits with a subscription model to ensure continuity of absorbent article delivery.

Preferably, the detection device comprises a battery and an internal clock, and wherein the life of the battery is greater than the predetermined time period, and wherein the predetermined time period is determined by said internal clock after the detection device (70) is first activated. Advantageously, the battery is still capable to operate the receiver such that as soon as a signal (e.g. relating to a confirmation trigger that a subscription has been activated or renewed) is received by the detection device is configured to reset the internal clock and continue operability and functionality.

In an embodiment, the battery is re-chargeable, preferably by wireless means, and wherein the internal clock is in electrical communication with a switch that powers off the detection device once the predetermined time period has lapsed and typically further in electrical communication with a second switch that prevents the battery to be re-charged, preferably wherein the predetermined time period is remotely reset upon response to an incoming signal wherein said incoming signal is triggered by an event such as selected from the group consisting of a renewal of a non-existing or expired subscription, an automatic renewal of a subscription, a confirmation that a subscription is still active, and combinations thereof. Advantageously, this allows to promote continuity in the subscription in a more environmentally friendly way compared to for example limiting the predetermined period by battery life of a non-rechargeable or non-replaceable battery and force users to purchase a new detector device each time the battery depletes and/or receive a free one each time an active subscription is made.

In any of the embodiments, the indicators herein may comprise an electrically conductive ink arranged in a pattern comprising a plurality of open circuits each corresponding to different positions of an absorbent core, said ink being printed on a skin-facing surface of the backsheet, wherein in response to a voiding event (or presence of exudates) a change in resistance is triggered within one or more of the circuits corresponding to the position of the voiding event. The pattern comprises a plurality of converging connection ends wherein each of said connection ends being adapted to come into electrical communication with corresponding connection terminals on the detection device when coupled to the absorbent article. The detection device typically comprising a battery, processor, a memory and a transmitter in order to process the triggered change in resistance and generate a signal to be sent to a further processing device (such as a computing device or a processing algorithm stored in the cloud).

In a preferred embodiment, the indictor 60 is an electrically conductive sensor (typically said sensor comprising a plurality of conductive tracks as described hereinabove) adapted to change one or more of its electrical properties in response to a voiding event such as presence of exudates in the absorbent article. Preferably, wherein the one or more electrical properties are selected from the group consisting of resistance, capacitance, inductance, and combinations thereof.

In an embodiment, the indicator 60 is adapted to detect each voiding event of a plurality of, typically sequential, voiding events throughout a wearing period of said absorbent article by a wearer. Advantageously, this allows for accurate monitoring of voiding pattern and behaviours with time to a degree that is not possible with standard color changing wetness indicators whereby once the color changes in response to a voiding event it fails to detect and differentiate any subsequent voiding events. Therefore, when the indicator comprises a color changing indicator it also comprises an electrically conductive sensor as described herein.

Preferably, the detection device 70 is adapted to recognize and distinguish each voiding event from each other voiding event immediately preceding and/or following the same, and preferably to cumulatively store a plurality of such events prior to transmitting a data set or data package to a processing device and/or computing means. Advantageously this allows to build a complete voiding pattern database that my be used to build a voiding pattern predictor and model.

The Stock Management System

Advantageously, the absorbent articles, kits and systems herein may allow for automatic inventory management in a household or even within institutional care.

In an embodiment, the system for monitoring an absorbent article and providing stock management functionality comprises: an absorbent article comprising: a liquid permeable topsheet 22, a liquid impermeable backsheet 24, and an absorbent core 20 positioned between said topsheet 22 and backsheet 24; an indicator 60 for indicating the presence of exudates, said indicator 60 being positioned on a body-facing side of said backsheet 24, the indicator 60 comprising a color-changing indicator and/or an electrically conductive indicator (such as an electrically conductive ink); a detection device 70 that can be removably attached to the absorbent article and arranged to detect a change in condition of said indicator 60; a computing means, such as a computing device or a computing algorithm typically stored on the cloud, arranged to deduct a one integer from a previous number n totaling the number of absorbent articles (typically in a stock or inventory of absorbent articles in a household or institution), including the one being used, (i.e. an inventory value) to generate a new number n−1 (i.e. an actual inventory value) representing the total number of absorbent articles left within an inventory (i.e. an inventory value), in response to at least one, preferably at least two, preferably only one, of the following: a signal from the detection device 70 triggered by a change in the state of the absorbent article such as from dry to wet; a signal from the detection device 70 triggered by a first-time connection to an absorbent article; and a signal from the detection device 70 triggered by disconnection of the detection device 70 from an absorbent article after a first-time connection to the absorbent article, and wherein the computing means is arranged to send a signal once the actual inventory value reaches a predefined threshold, wherein said signal triggers at least one of: a warning alarm (typically said alarm being triggered by the detection device or a mobile device as described in more detail hereinbelow); an automatic order of new stock comprising a plurality of new absorbent articles; and combinations thereof (by "new" it is meant herein an unused plurality of clean absorbent articles). Advantageously, this arrangement allows a user (or care giver) to be automatically notified when the stock of absorbent articles is running out well in advance to ensure replenishment without having to keep excessive stock within the household or institution and thus better manage supply chain based on needs and consumption. It is particularly advantageous to build an effective subscription model infrastructure where new deliveries of stock can be automated based on use rather than based on time period, hence providing a more flexible service to users and care givers based on the needs.

In an embodiment, the detection device 70 has features as described in embodiments herein.

In an embodiment, the detection device comprises a transmitter arranged to transmit signals to the computing means, preferably an algorithm or logic stored on a cloud-based server. Advantageously, this allows to save battery power and processing power of the detection device in order to limit the size and cost thereof. Preferably the clip-on unit and the incontinence management system is arranged as described in co-pending application EP19178665.6, especially page 43 line 27 to page 57 line 28, herein incorporated by reference.

Figure 22:
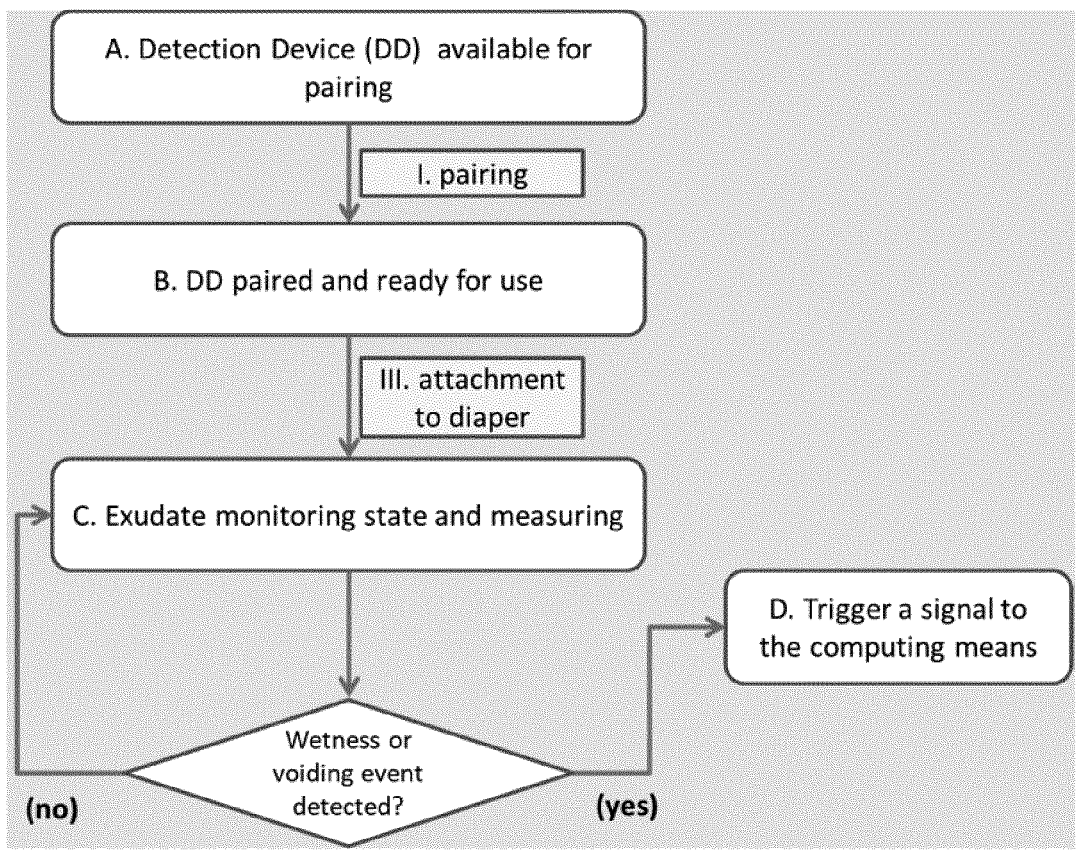
FIG. 22 is a schematic representation of part of a process flow according to embodiments herein.

As illustrated in exemplary FIG. 22, following an optional pairing step, the detection device that is connected to the diaper begins to monitor for changes in status of the indicator (whether optical changes in case of a color changing indicator or electrical changes, such as resistance, in case of an electrically conductive indicator) and as soon as a wetness or voiding event is detected (such as exudates being present in the diaper) a signal is sent to the computing means to deduct an absorbent article from the total number of absorbent articles in an inventory or stock (such as an inventory or stock of absorbent articles in a household or institution).

Figure 23:
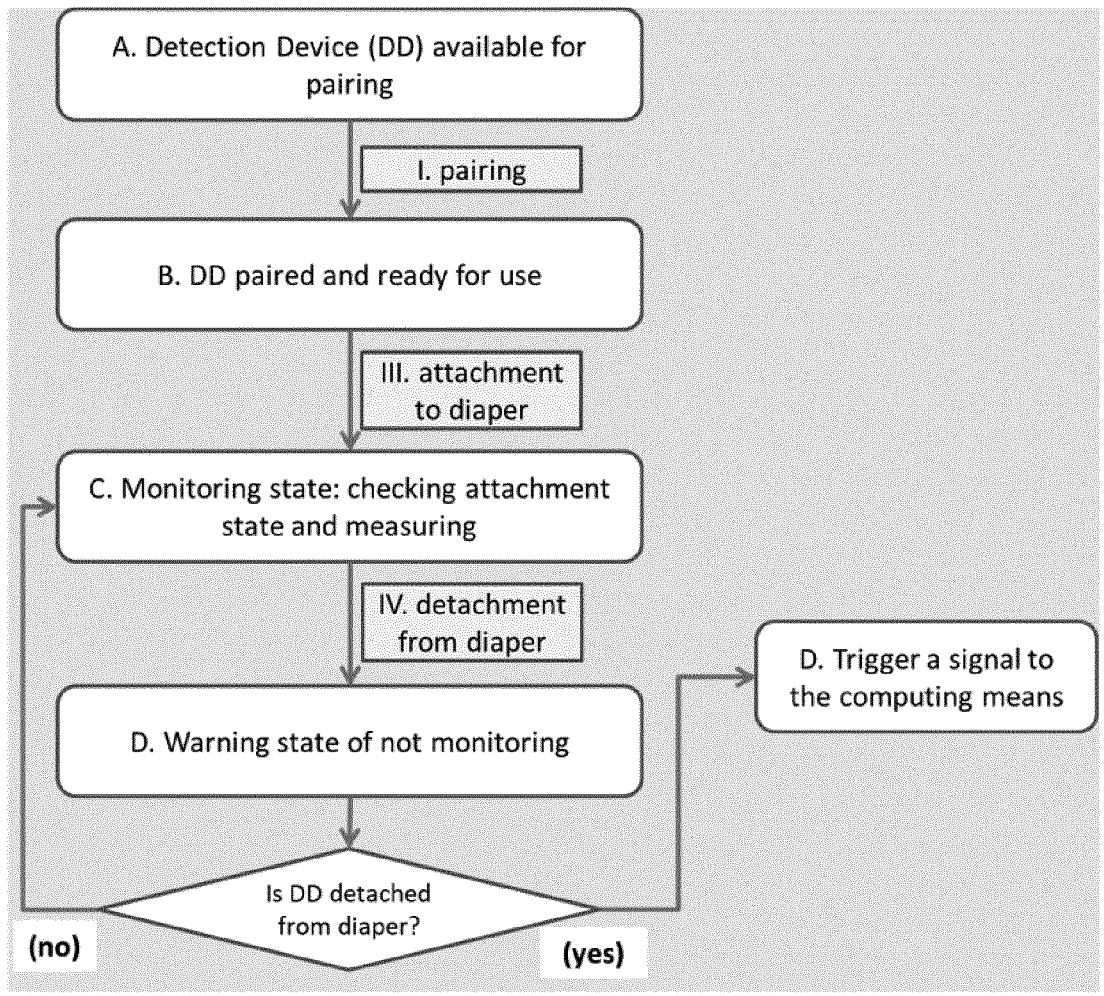
FIG. 23 is a schematic representation of part of a process flow according to embodiments herein.

As illustrated in exemplary FIG. 23, following an optional pairing step, the detection device that is connected to the diaper begins to monitor for changes in status of the indicator and also the attachment state to the diaper (i.e. whether attached or not attached). The latter may be done by for example checking the presence of one of several, typically three, predetermined colors of the indicator (e.g. yellow, green or blue, in case a color changing indicator is used as described above that changes from yellow in dry state to blue in wet state) typically via the optical sensor; or a predetermined resistance when the indicator comprises one or more electrically conductive sensor tracks (such as a printed pattern with a conductive ink), and once a change is detected, such as a color different from the predetermined colors or the resistance increases to above said predetermined resistance, then a signal to the computing means is triggered to deduct an absorbent article from the total number of absorbent articles in an inventory or stock (such as an inventory or stock of absorbent articles in a household or institution).

In an embodiment, the system for monitoring an absorbent article and providing stock management functionality comprises: an absorbent article comprising an optical property changing indicator adapted to change at least one optical property in response to the presence or absence of exudates, wherein the absorbent article and the indicator form one integral unit; a detection device comprising a housing, a battery, a transmitter and a receiver disposed within the housing, an optical sensor disposed within the housing, and at least two powered light sources disposed within the housing and spaced from the optical sensor, the optical sensor adapted to detect the change of the optical property of the indicator, wherein at least one of the absorbent article and the detection device is adapted to be associated together and disassociated from each other, wherein when the absorbent article and the detection device are associated together the light source emits light in a direction towards the absorbent article and the detection device is adapted to detect the change of optical property of the indicator in response to the presence or absence of exudates, wherein the at least two light sources comprise a first light source and a second light source being of different colors, preferably a Blue light source and a Red light source, and wherein each time the detection device detects a change in the state of the absorbent article such as from dry to wet, the detector device sends a signal to a computing device that is arranged, in response thereto, to deduct a one integer from a previous number n totaling the number of absorbent articles, including the one being used, to generate a new number n−1 representing the total number of absorbent articles left within an inventory, and preferably wherein the computing device sends a signal once the inventory value reaches a predefined threshold, wherein said signal is selected from the group consisting of (or triggers one or more of): a warning alarm, an automatic order of new stock comprising a plurality of new absorbent articles, and combinations thereof. Advantageously, this allows for a simple and effective way to manage an inventory without complex systems requiring recognizing of connection/decoupling of the detection device or other means to recognize when an absorbent article such as a diaper is being disposed of to track how many are left from a given stock. Indeed, the principle is that as soon as a voiding event happens, the diaper will at some point need to be replaced and for systems that are already designed to detect wetness events further linking an inventory management to specifically the voiding event leads to a reliable inventory tracking.

Figure 24:
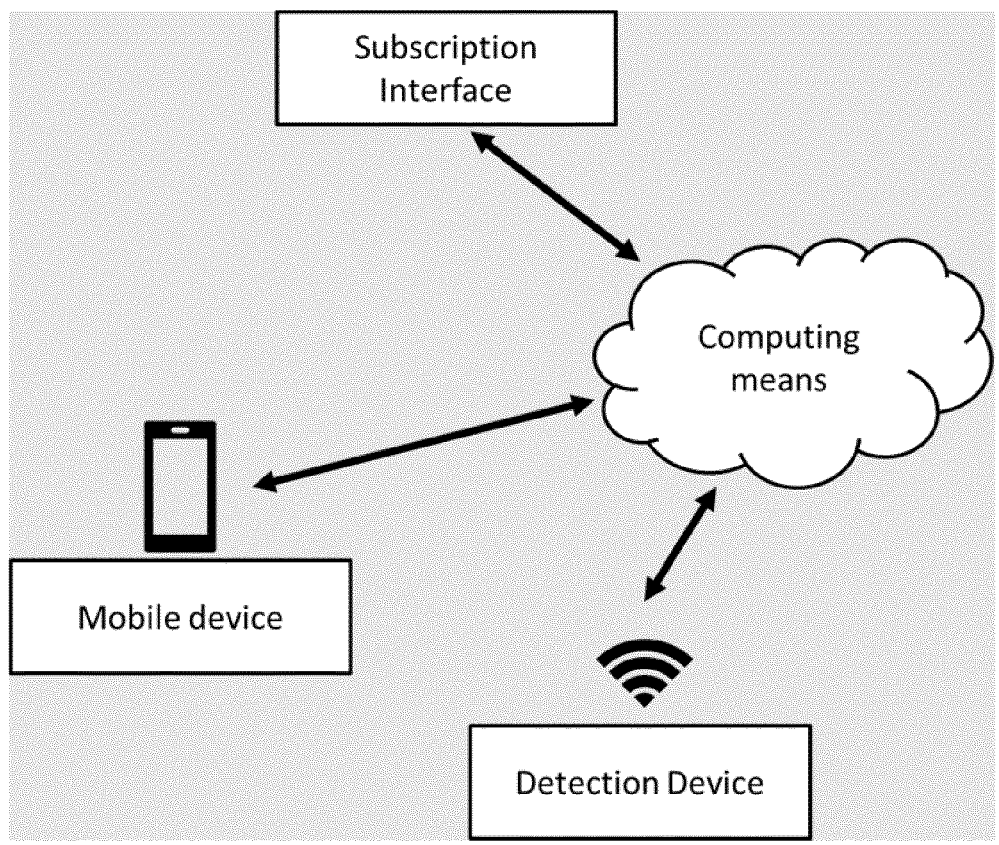
FIG. 24 is a schematic representation of a system according to embodiments herein.
Figure 25:
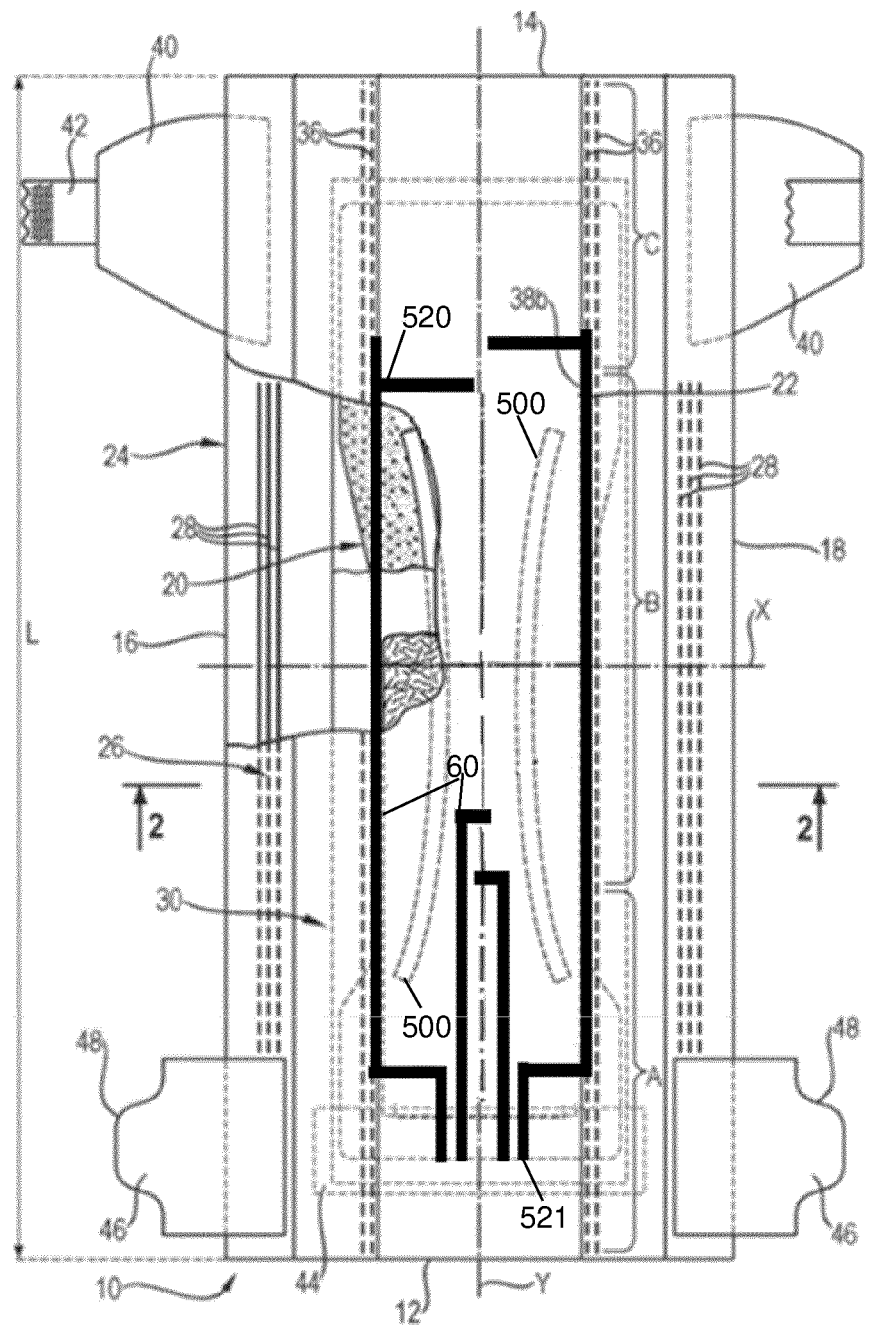
FIG. 25 is a top view of an absorbent article according to an embodiment of the present disclosure in the form of a diaper with some layers partially removed.

In an embodiment, as exemplary shown in FIG. 24, the systems herein further comprise a mobile device such as a smartphone comprising an application with a user interface, and wherein at least an initial inventory value n is manually set by the user or caregiver such as when replenishing a stock comprising a plurality of absorbent articles in a household or institution via said mobile device, preferably wherein the mobile device is in wireless data communication with the computing means. Advantageously this allows users and caregivers to directly interact with the stock management system.

In an embodiment, the inventory value n is automatically reset upon delivery of a new stock comprising a plurality of new absorbent articles, that are delivered within a subscription, typically following a respective signal sent from a subscription interface to the computing means. Advantageously this allows for a usage based subscription model to be optimally implemented rather than classic time-based subscription models for a more individualized and user-focused experience.

In an embodiment, once the actual inventory value reaches a predetermined threshold, such as a number from 10 to 40, the computing means is arranged to send a signal to a subscription interface to release the next shipment of absorbent articles to replenish the stock of a plurality of absorbent articles in a respective household or institution that is associated with said actual inventory value.

Typically, one or more detection devices comprise a unique identifier that is associated to a household or institution, and typically wherein a plurality of metadata are associated with said unique identifier such as address and subscription status of the household or institution, and are typically retained in data transfer between the detection device(s) and the computing means. Preferably, wherein the computing means computes, updates and stores a plurality of inventory values for a plurality of households and/or institutions.

In an embodiment, the predetermined threshold is pre-set manually by a user via a mobile device application, and typically wherein the subscription interface is adapted to send a signal to the computing means and/or mobile device application to trigger a warning and a suggested new predetermined threshold in response to a delivery-affecting event such as upcoming national holiday(s), strike of postal delivery providers, delays in supply chain production and the like. Advantageously this allows the user or caregiver to choose to increase the predetermined threshold value in order to have sufficient stock to cope with the event.

Preferably, the mobile device application comprises a anticipated-delivery-request tab that when activated by a user or requestor (e.g. following such a warning as described above) triggers a signal to the subscription interface to deliver a new stock of absorbent articles even if the predetermined threshold is not reached.

In an embodiment, the application stores historical data comprising voiding events and patterns such that it may be consulted by a user or caregiver or a predictive model be generated based thereon.

The invention claimed is:

1. An absorbent article for personal hygiene, the absorbent article comprising:
    a liquid permeable topsheet (22);
    a liquid impermeable backsheet (24);
    an absorbent core (20) positioned between said topsheet (22) and backsheet (24),
    an indicator (60) for indicating the presence of exudates and being positioned on a body-facing side of said backsheet (24), the indicator (60) comprising an electrically conductive material,
    the article further comprising a detection device (70) that can be removably attached to the absorbent article such to become in electrical communication with said indicator (60) when attached to said article to measure a change in resistance or capacitance in response to a voiding event,
    characterized in that the absorbent core (20) comprises one or more channels (500) substantially free of absorbent material, and in that the indicator (60) comprises a pattern that extends inboard and/or outboard of said channel(s) such that it does not substantially overlap with said channel(s), wherein the pattern extends substantially parallel to at least a portion of said channel(s).

2. An absorbent article according to claim 1, wherein the absorbent core (20) comprises a core wrap (66) enclosing absorbent material therein and wherein a top layer (66a) of the core wrap (66) is joined to a bottom layer (66b) of the core wrap (66) to form one or more channels (500) substantially free of absorbent material.

3. An absorbent article according to claim 1, wherein the absorbent core (20) comprises a plurality of channels (500) comprising at least one right channel and at least one left channel, the right channel being disposed between the right side edge (18) and the longitudinal centreline along axis (Y), and the left channel being disposed between the left side edge (16) and the longitudinal centreline along axis (Y), wherein the right and left channels are arcuate in shape such that the front and back ends of the left and right channels diverge towards the left side edge (16) and the transversely opposed right side edge (18) respectively and wherein the central portion of said channels converge towards the longitudinal centreline along axis (Y); or wherein the absorbent core (20) comprises a single channel (500) comprising two parallel and opposing longitudinally extending portions and one transversely extending portion connecting said longitudinally extending portions to form a substantially U-shaped channel (500).

4. An absorbent article according to claim 1, wherein the pattern of the indicator (60) comprises a plurality of sensing tracks (520) each track forming an open circuit corresponding to a different position of the backsheet (24) and the absorbent core (20) such that voiding events in said different positions may be individually monitored.

5. An absorbent article according to claim 4, wherein each of the sensing tracks (520) comprises a connection end (521) arranged to couple to a respective terminal end of the detection device (70) to form an electrical connection between said detection device (70) and said sensing tracks (520) of the indicator.

6. An absorbent article according to claim 4 wherein the sensing tracks (520) are printed with a conductive ink, wherein the conductive ink is a carbon-based ink and/or a conductive polymer-based ink.

7. An absorbent article according to claim 6 wherein the conductive polymer-based ink comprises a polymer selected from the group consisting of poly(pyrrole) s (PPY), polyanilines (PANI), poly(thiophene) s (PT), poly(p-phenylene sulfide) (PPS), poly(p-phenylene) (PPP), Poly(acetylene) s (PAC), Poly(p-phenylene vinylene) (PPV), poly(3,4-ethylenedioxythiophene) (PEDOT), and mixtures thereof.

8. An absorbent article according to claim 6 wherein the conductive polymer-based ink comprises poly(3,4-ethylenedioxythiophene) polystyrene sulfonate (PEDOT:PSS).

9. An absorbent article according to claim 6 wherein the carbon-based ink comprises a conductive compound selected from the group consisting of graphene, graphite, nano-carbon-tubes and mixtures thereof.

10. An absorbent article according to claim 6 wherein the conductive polymer-based ink comprises a polymer selected from the group consisting of polyacetylene, polypyrrole, polyaniline and copolymers thereof.

11. An absorbent article according to claim 1, wherein the indicator (60) is free of metals.

12. An absorbent article according to claim 1, wherein the indicator (60) further comprises a color-changing indicator.

13. An absorbent article according to claim 12 wherein the detection device (70) further comprises an optical sensor and one or more light sources.

14. An absorbent article according to claim 1, wherein the indictor (60) is an electrically conductive sensor adapted to change one or more of its electrical properties in response to a voiding event in the absorbent article.

15. An absorbent article according to claim 14 wherein the one or more electrical properties are selected from the group consisting of resistance, capacitance, inductance, and combinations thereof.

16. An absorbent article according to claim 14 wherein the indicator (60) is adapted to detect each voiding event of a plurality of voiding events throughout a wearing period of said absorbent article by a wearer.

17. An absorbent article according to claim 16 wherein the detection device (70) is adapted to recognize and distinguish each voiding event from each other voiding event immediately preceding and/or following the same, and to cumulatively store a plurality of voiding events prior to transmitting a data set or data package to a processing device and/or computing means.

* * * * *